US008877800B2

(12) United States Patent
Mangel

(10) Patent No.: US 8,877,800 B2
(45) Date of Patent: *Nov. 4, 2014

(54) KAPPA-OPIATE AGONISTS FOR THE TREATMENT OF DIARRHEA-PREDOMINANT IRRITABLE BOWEL SYNDROME

(75) Inventor: Allen Mangel, Chapel Hill, NC (US)

(73) Assignee: Tioga Pharmaceuticals, Inc., San Diego, CA (US)

( * ) Notice: Subject to any disclaimer, the term of this patent is extended or adjusted under 35 U.S.C. 154(b) by 633 days.

This patent is subject to a terminal disclaimer.

(21) Appl. No.: 12/940,979

(22) Filed: Nov. 5, 2010

(65) Prior Publication Data

US 2011/0046174 A1   Feb. 24, 2011

Related U.S. Application Data

(63) Continuation of application No. 12/044,906, filed on Mar. 7, 2008, now Pat. No. 7,960,429.

(60) Provisional application No. 60/920,841, filed on Mar. 30, 2007.

(51) Int. Cl.
*A61K 31/40* (2006.01)

(52) U.S. Cl.
USPC .......................................... 514/424

(58) Field of Classification Search
USPC .......................................... 514/424
See application file for complete search history.

(56) References Cited

U.S. PATENT DOCUMENTS

| | | | |
|---|---|---|---|
| 4,192,883 A | 3/1980 | Cousse | |
| 4,663,343 A | 5/1987 | Horwell et al. | |
| 4,760,069 A | 7/1988 | Rzeszotarski et al. | |
| 4,806,547 A | 2/1989 | Giardina et al. | |
| 4,889,860 A | 12/1989 | Rzeszotarski et al. | |
| 5,091,392 A | 2/1992 | Raddatz et al. | |
| 5,232,978 A | 8/1993 | Gottschlich et al. | |
| 5,389,686 A | 2/1995 | Diop et al. | |
| 5,532,266 A | 7/1996 | Gottschlich et al. | |
| 5,585,500 A | 12/1996 | Drauz et al. | |
| 5,776,972 A | 7/1998 | Barber et al. | |
| 5,977,161 A | 11/1999 | Barber et al. | |
| 6,060,504 A | 5/2000 | Stein et al. | |
| 6,194,454 B1 | 2/2001 | Dow | |
| 6,329,403 B1 | 12/2001 | Odaka et al. | |
| 6,344,566 B1 | 2/2002 | Bathe et al. | |
| 6,562,363 B1 | 5/2003 | Mantelle et al. | |
| 6,569,449 B1 | 5/2003 | Swaan et al. | |
| 7,164,021 B2 | 1/2007 | Welsh et al. | |
| 7,563,899 B2 | 7/2009 | Boyd et al. | |
| 2001/0051181 A1 | 12/2001 | Van Osdol et al. | |
| 2002/0025948 A1 | 2/2002 | Banks et al. | |
| 2003/0036546 A1 | 2/2003 | Clemens | |
| 2004/0157913 A1 | 8/2004 | Jacob et al. | |
| 2004/0266806 A1 | 12/2004 | Sanghvi et al. | |
| 2005/0004155 A1 | 1/2005 | Boyd et al. | |
| 2005/0176746 A1 | 8/2005 | Weber et al. | |
| 2006/0122255 A1 | 6/2006 | Wiesner et al. | |
| 2007/0010450 A1 | 1/2007 | Currie et al. | |

FOREIGN PATENT DOCUMENTS

| | | |
|---|---|---|
| CA | 2006413 | 6/1990 |
| CA | 2054648 | 5/1992 |
| CA | 2179955 | 12/1996 |
| CN | 1081631 C | 3/2002 |
| CN | 1767830 | 5/2006 |
| CN | 1767831 | 5/2006 |
| CN | 101677997 | 3/2010 |
| DE | 195 23 502 | 1/1997 |
| DE | 198 49 650 | 5/2000 |
| EP | 0 330 467 | 2/1989 |
| EP | 0 569 802 | 11/1993 |
| EP | 0 761 650 B1 | 10/2001 |
| EP | 0 752 246 B1 | 3/2002 |
| EP | 1 073 634 B1 | 8/2005 |
| FR | 2421891 | 10/1977 |
| JP | 2000-80047 | 3/2000 |
| JP | 2000-256299 | 9/2000 |
| JP | 2001-517493 | 10/2001 |
| RU | 96112771 | 9/1998 |
| WO | WO-91/08205 | 6/1991 |
| WO | WO-91/08206 | 6/1991 |
| WO | WO-01/98267 | 12/2001 |
| WO | WO-02/13801 | 2/2002 |
| WO | WO-03/048113 | 6/2003 |
| WO | WO-2004/091622 | 10/2004 |
| WO | WO-2004/091623 | 10/2004 |
| WO | WO-2005/046687 | 5/2005 |
| WO | WO-2008/121496 | 10/2008 |

OTHER PUBLICATIONS

Barber et al., B. J. Pharmacol. (1994) 113:1317-1327.
Barber and Gottschlich, Expert Opin. Invest. Drugs (1997) 6(10):1351-1368.
Bardhan et al., Aliment Pharamacol. Ther. (2000) 14:23-34.
Bhargava et al., Brain Research (1993) 625(1):120-124.
Binder et al., Anesthesiology (2001) 94:1034-1044.
Boeckxstaens et al., The Am. J. of Gastroenterology (2002) 91:1.
Burton and Gebhart, J. Pharmacol. Exp. Ther. (1998) 285:707-715.
CA78(9) 58099r, Clemence et al., FR 2113786 patent abstract Aug. 1972.
CA77(11) 75024, Clemence et al., DE 2155906 patent abstract May 1972.
Camilleri et al., Arch. Intern. Med. (2001) 161(14):1733-1740.
Camilleri et al., Lancet (2000) 355(9209):1035-1040.
Camilleri, Current Opinion in Pharmacology (2008) 8:671-676.

(Continued)

*Primary Examiner* — Raymond Henley, III
(74) *Attorney, Agent, or Firm* — Morrison & Foerster LLP

(57) ABSTRACT

The present invention concerns methods useful in treating a subject having diarrhea-predominant IBS (IBS-D) by administering N-methyl-N-[(1S)-1-phenyl-2-((3S)-3-hydroxypyrrolidin-1-yl)ethyl]-2,2-diphenylacetamide and/or a pharmaceutically acceptable salt thereof to the subject.

20 Claims, 17 Drawing Sheets

(56) References Cited

OTHER PUBLICATIONS

Camilleri et al., Gastroenterology (2008) 135:1877-1891.
Camilleri, Neurogastroenterol Motil (2008) 20:971-979.
Chang et al., Current Treatment Options in Gastroenterology (2006) 9:314-323.
Choung et al., Program of the Annual Meeting of the American Gastroenterlogical Association and Digestive Disease Week, May 19-24, 2007, AGA Abstracts, M1154, p. A-373.
Choung et al., Asimadoline for FD Poster (2007).
Corazziari, Can. J. Gastroenterol. (1999) 13(Suppl A):71A-75A.
Coulie et al., Gastroenterology (2000) 119:41-50.
Dehaven-Hudkins et al., J. Pharmacol. Exp. Ther. (1999) 289(1):494-502.
Delgado-Aros et al., Current Treatment Options in Gastroenterology (2004) 7:121-131.
Delgado-Aros et al., Am. J. Physiol. Gastrointest. Liver Physiol. (2003) 284:G558-G566.
Delgado-Aros et al., Gastroenterology (2002) 122:A-59.
Delvaux et al., Aliment Pharmacol. Ther. (2004) 20:237-246.
Delvaux, Expert Opin. Investig. Drugs (2001) 10(1):97-110.
Encyclopedia of Medicaments M. RLS, 2001, pp. 583-585 and 1067-1068 (English Translation only).
Endoh et al., Life Sci. (1999) 65(16):1685-1694.
Gevaerd et al., Braz. J. Med. Biol. Res. (1999) 32(12):1545-1550.
Glazer, Arch. Intern. Med. (2001) 161(15):1814-1824.
Gottschlich et al., Bioorganic & Medicinal Chemistry Letters (1994) 4(5):677-682.
Gottschlich et al., Chirality (1994) 6:685-689.
Gottschlich et al., Drugs Exptl. Clin. Res. (1995) XX(5):171-174.
Hahn et al., Dig. Dis. Sci. (1998) 43:2715-2718.
Hasler, "Disorders of Gastric Emptying," in: Textbook of Gastroenterology, 3rd edition, Yamada (ed.), Lippincott Williams & Wilkins, Philadelphia (1999) Ch. 63, pp. 1341-1369.
Heaton et al., Gut (1991) 32(1):73-79.
Hendrickson et al., Clin. Microbiology Reviews (2002) 79-94.
Hendrickson et al., Organic Chemistry $3^{rd}$. ed. (1970) p. 513.
Holtmann et al., Am J. Gastroenterol. (1997) 92:954-959.
International Search Report for PCT/US08/56317, mailed on Jun. 24, 2008, 2 pages.
Isselbacker et al., "Harrison's Principles of Internal Medicine" vol. 2, Thirteenth ed. (1994) pp. 1403-1417.
Jarosz et al., Biol. Res. Nurs. (2002) 3(4):198-209.
Johnson, Medical Hypotheses (1995) 45(5):491-497.
Joshi et al., J. Neurosci. (2000) 20(15):5874-5879.
Lemcke et al., European Journal of Pharmacology (1991) 193:109-115.
Longstreth et al., Gastroenterology (2006) 130(5):1480-1491.
Mangel et al., Aliment Pharmacol Ther (2008) 28:239-249.
Mangel et al., Neurogastroenterol Motil (2008) 20:1086-1093.
Mayer and Gebhart, Basic and Clinical Aspects of Chronic Abdominal Pain, vol. 9, First Edition, Amsterdam: Elsevier, 1993, pp. 3-28.
Mendelson, American Journal of Psychiatry (2001) 158(6):963-964.
Morley et al., American Journal of Clinical Nutrition (1985) 42(6):1175-1178.
Morley et al., Life Sciences (1982) 31:2617-2626.
Morley and Levine, Peptides (1983) 4:797-800.

Nemmani and Ramarao, Life Sci. (2002) 70(15):1727-1740.
Olden, Cleveland Clinic J. Med. (2003) 70(Suppl 2):S3-S7.
Patrick et al., Dig. Dis. Sci. (1998) 43:400-411.
Quigley, Expert Opinion on Pharmacotherapy (2000) 1:881-887.
Ramabadran, European Journal of Pharmacology (1984) 98(3-4):425-427.
Read et al., Gut (1997) 41:664-668.
Riviere et al., Acta. Neurobiol. Exp. (1999) 59:186.
Roger et al., Can. J. Vet. Res. (1994) 58(3):163-166.
Rogers et al., Br. J. Pharmacol. (1992) 106(4):783-789.
Sandner-Kiesling et al., Pain (2002) 96(1-2):13-22.
Schmidt, Am. J. Surg. (2001) 182(Suppl 5A):27S-38S.
Shook et al., Journal of Pharmacology and Experimental Therapeutics (1989) 249:83-90.
Stachura and Herman, Pol. J. Pharmacol. (1994) 46(1-2):37-41.
Supplementary European Search Report for EP 08 73 1748, mailed on Apr. 27, 2010, 9 pages.
Suzuki et al., Biol. Pharm. Bull. (1997) 20(11):1193-1198.
Szarka et al., Clinical Gastroenterology and Hepatology (2007) 5:1268-1275.
Szarka et al., Program of the Annual Meeting of the American Gastroenterlogical Association and Digestive Disease Week, May 19-24, 2007, AGA Abstracts, W1213, p. A-684.
Talley et al., Aliment Pharmacol Ther (2008) 27:1122-1131.
Tarayre et al., Arzneim-Forsch./Drug Res. (1983) 33(II)7:931-935.
The Merck Manual, $17^{th}$ edition (1999), pp. 312-313.
Tortella et al., Journal of Pharmacology and Experimental Therapeutics (1997) 282(1):286-293.
Trimble et al., Dig. Dis. Sci. (1995) 40:1607-1613.
Upton et al., European Journal of Pharmacology (1982) 78(4):421-429.
Walsh et al., Psychopharmacology (2001) 157(2):151-162.
Winter et al., "Effects of mu- and kappa-opiod receptors on postoperative ileus in rats", Eur. J. Pharmacol. (1997) 339(1):63-67.
Written Opinion of the International Searching Authority for PCT/US08/56317, mailed on Jun. 24, 2008, 4 pages.
Yan and Roth, Life Sci. (2004) 75:2615-2619.
Zigmond and Snaith, Acta Psychiatr. Scand. (1983) 67(6):361-370.
Zviaginzeva, Irritable bowel syndrome, medical newspaper Health of Ukraine, No. 73, Jun. 2003 (machine translation), online at http://health-ua.com/articles/245.html.
Office Action for CA 2,682,608, mailed Nov. 12, 2013, 5 pages.
European Search Report for EP 12182095.5, mailed Jan. 30, 2013.
First Office Action (English translation) for CN 200880017324.9, issued Jul. 13, 2011, 3 pages.
First Office Action (including English translation) for CN 201210113405.7, issued Apr. 15, 2013.
Adams and Bresnick, On Call Surgery, second edition (Jan. 15, 2001), Saunders (London), pp. 1, 2, and 285.
Pharmateka No. 3 online publication: yandex:http://www.pharmateca.ru/cgi-bin/statyi.pl?sid=669&mid=1085056555&magid=55&full=1/, retrieved on Sep. 26, 2007.
Office Action in EP 08731748.3, mailed Mar. 17, 2011, 4 pages.
Office Action (including translation) in RU 2009140042, mailed Apr. 11, 2011, 8 pages.
Zviaginzeva, Irritable bowel syndrome, medical newspaper Health of Ukraine, No. 73, Jun. 2003, online at http://health-ua.com/articles/245.html.

FIGURE 3
Proportion of Months with Adequate Relief of IBS Pain or Discomfort
All IBS subjects with baseline pain score ≥2.0
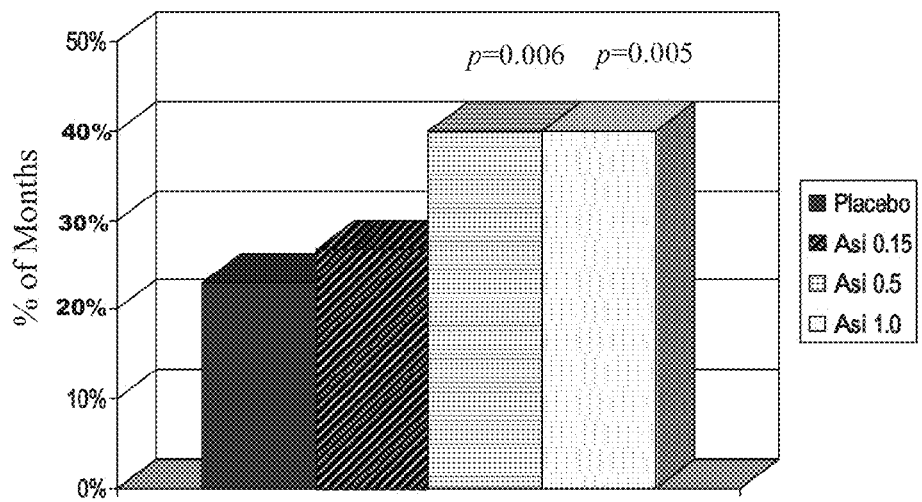
IBS-D subjects with baseline pain score ≥2.0
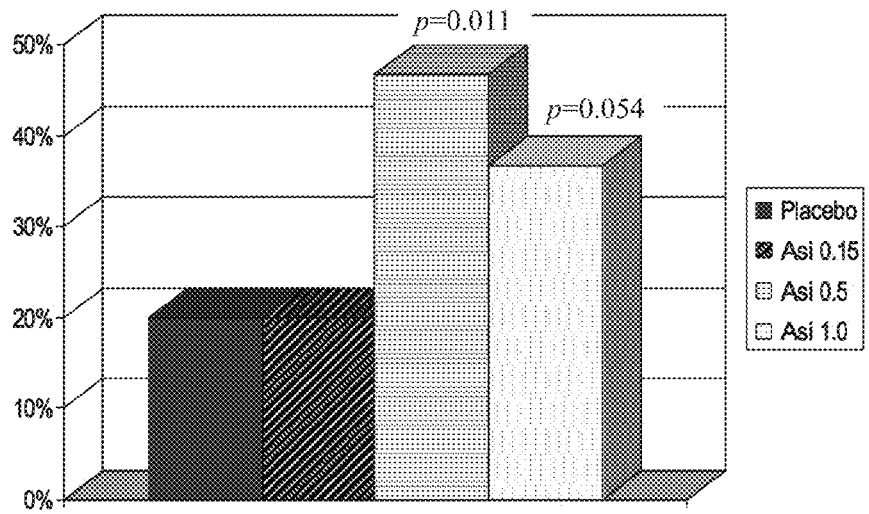

Weekly Effect of Asimadoline on Adequate Relief of IBS Pain or Discomfort

Proportion of Months with Adequate Relief of IBS Pain or Discomfort

Percent of Pain Free Days During Weeks 1-12 in IBS-D subjects with baseline pain score ≥2.0

Proportion of Months with Adequate Relief of IBS Pain or Discomfort

Monthly and Weekly Changes in IBS Pain Scores
IBS-D subjects with baseline pain score ≥2.0

Monthly Responders Reporting Adequate Relief of IBS Pain or Discomfort

Proportion of Months with Adequate Relief of IBS Symptoms

FIGURE 14
Monthly Change in Stool Consistency
A     IBS-D subjects with baseline pain score ≥2.0
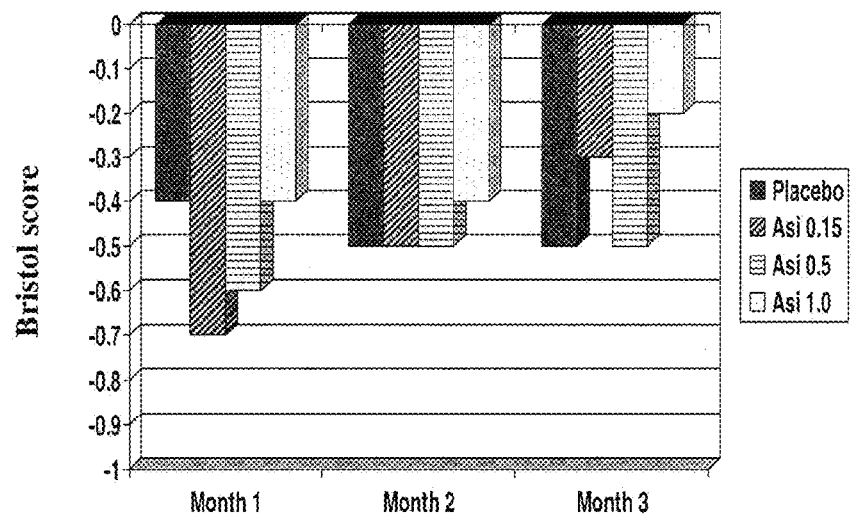
B     IBS-C subjects with baseline pain score ≥2.0
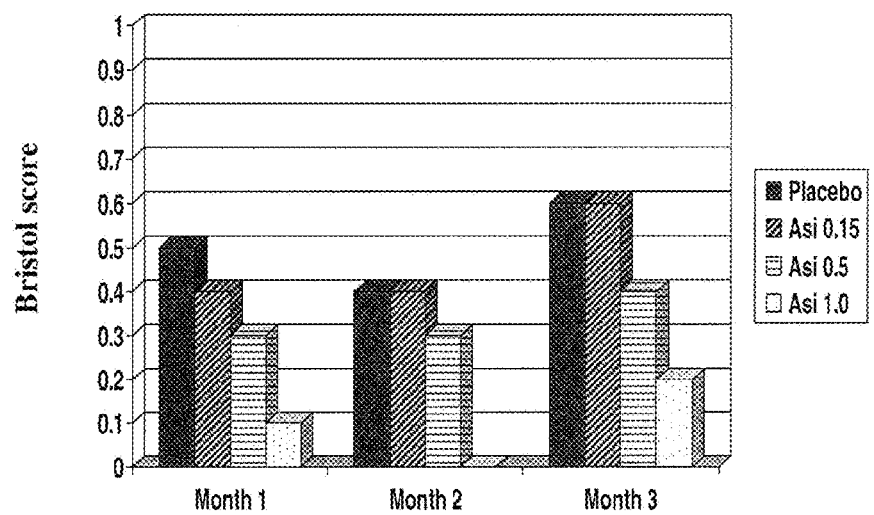

KAPPA-OPIATE AGONISTS FOR THE TREATMENT OF DIARRHEA-PREDOMINANT IRRITABLE BOWEL SYNDROME

CROSS-REFERENCE TO RELATED APPLICATIONS

This application claims priority to U.S. patent application Ser. No. 12/044,906, filed Mar. 7, 2008, now U.S. Pat. No. 7,960,429, which claims priority to U.S. Provisional Patent Application Ser. No. 60/920,841, filed Mar. 30, 2007, the contents of which are hereby incorporated by reference in its entirety.

TECHNICAL HELD

The present invention concerns methods useful in treating irritable bowel syndrome (IBS), and particularly one or more subtypes thereof, and is useful for treating diarrhea. More specifically, the invention relates to the use of peripherally selective kappa opiate agonists, especially N-methyl-N-[(1S)-1-phenyl-2-((3S)-3-hydroxypyrrolidin-1-yl)ethyl]-2,2-diphenylacetamide or a pharmacologically acceptable salt thereof for the preparation of medicaments for the treatment of diarrhea, or for the treatment of IBS, in particular IBS with predominant diarrhea (IBS-D) and IBS with alternating constipation and diarrhea (IBS-A), and the pain and/or discomfort associated therewith.

BACKGROUND OF THE INVENTION

IBS affects approximately 10-15% or more of the general population. It is the most common disease diagnosed by gastroenterologists and one of the most common disorders seen by primary care physicians. IBS has also been referred to as spastic colon, mucous colitis, spastic colitis, nervous stomach, or irritable colon.

Irritable bowel syndrome is characterized by a group of symptoms in which abdominal pain or discomfort is associated with a change in bowel pattern, such as loose or more frequent bowel movements, diarrhea, and/or constipation.

Irritable bowel syndrome is understood as a multi-faceted disorder. In people with IBS, symptoms result from what appears to be a disturbance in the interaction between the gut or intestines, the brain, and the autonomic nervous system that alters regulation of bowel motility (motor function) or sensory function.

Although the pathophysiology of IBS is incompletely understood, visceral hypersensitivity is thought to have an important role (Holtmann et al. (1997) *Am. J. Gastroenterol.*, 92, 954-959; Trimble et al., (1995) *Dig. Dis. Sci.*, 40, 1607-1613). For example, patients and control subjects were evaluated for their pain thresholds in response to progressive distension of the sigmoid colon induced by a balloon. At the same volume of distension, the patients reported higher pain scores compared to control subjects. This finding has been reproduced in many studies. There are two aspects to visceral hypersensitivity, hyperalgesia and allodynia. Hyperalgesia refers to the situation in which normal visceral sensations are experienced at lower intraluminal volumes. Allodynia refers to the situation where pain or discomfort is experienced at volumes usually producing normal internal sensations (see, for example, Mayer & Gebhart, Basic and Clinical Aspects of Chronic Abdominal Pain, Vol. 9, 1 ed. Amsterdam: Elsevier, 1993:3-28). In animal models, asimadoline has been shown to reduce sensation responses to gastric and colon distention (Burton & Gebhart (1998) *J. Pharmacol. Exp. Ther.*, 285, 707-715), but there is no reason to suspect that asimadoline would selectively benefit one or more subtypes of IBS.

Treatment options for IBS generally include multiple approaches customized to each patient depending upon the severity of the symptoms and the IBS subtype. Patients diagnosed with mild IBS symptoms may be counseled about managing stress and making diet and lifestyle changes. Patients diagnosed with moderate IBS are similarly counseled with the added recommendation of fiber supplements. Depending on the symptoms, moderate IBS patients can also be advised to use antidiarrheals, laxatives, or anticholinergic agents. Typical antidiarrheals include loperamide, attapulgite, and diphenoxylate. Typical laxatives include bisacodyl, senna, polyethylene 3350, and bulk-forming fiber laxatives, such as psyllium, calcium polycarbophil, methylcellulose, and fructan. An example of an anticholinergic used in treating IBS is dicyclomine.

Patients diagnosed with severe IBS may also receive treatment with antidepressants, such as tricyclics and selective serotonin reuptake inhibitors. Severe IBS may also be treated with alosetron or tegaserod.

Alosetron is a $5\text{-}HT_3$ antagonist used for the management of severe IBS-D in women only. It acts on the $5\text{-}HT_3$ receptors of the enteric nervous system of the gastrointestinal tract and is thought to relax the colon and slow the movement of waste through the lower bowel. Notably the drug was removed from the market just nine months after its approval when it was linked to at least four deaths and severe side effects in 197 people. In June 2002, the Food and Drug Administration (FDA) decided to allow alosetron to be sold again with restrictions. The drug can be prescribed only by doctors enrolled in a special program and is intended for severe cases of IBS-D in women who haven't responded to other treatments. It is not approved for use by men.

Tegaserod is a $5\text{-}HT_4$ agonist used for the management of Constipation-predominant IBS (IBS-C) in women. It is a motility stimulant. Therapeutic effect is achieved through activation of 5-HT4 receptors of the enteric nervous system in the gastrointestinal tract. Tegaserod stimulates gastrointestinal motility and the peristaltic reflex, and possibly also reduces abdominal pain. It has been linked to episodes of ischemic colitis. Tegaserod has not been approved for use in men. In 2007, tegaserod was withdrawn from the market due to increased risk of heart attack, stroke and unstable angina in patients taking tegaserod.

IBS patients with an alternating bowel habit pattern present a unique clinical challenge and many of the IBS medications being studied affect either diarrhea or constipation and thus may not be appropriate for IBS-A patients. There is currently no available pharmaceutical treatment for the management of IBS-A.

Thus, there is presently an unmet market need for a safe and efficacious therapeutic agent to treat one or more IBS subtypes in male and female patients.

Here, it has been surprisingly discovered that selective opiate receptor modulators, peripherally selective opiate receptor modulators, peripherally selective kappa-opiate receptor modulators, and peripherally selective kappa-opiate receptor agonists, N-methyl-N-[(1S)-1-phenyl-2-((3S)-3-hydroxypyrrolidin-1-yl)ethyl]-2,2-diphenylacetamide or pharmacologically acceptable salts thereof can be used for treating diarrhea, or one or more subtypes of IBS, and are particularly useful for the treatment of IBS-D and IBS-A.

All publications, patents, and patent applications cited herein are hereby incorporated by reference in their entirety.

SUMMARY OF THE INVENTION

The present invention provides novel methods useful in treating one or more subtypes of IBS. In one embodiment, the subtype is IBS-D. In another embodiment, the subtype is IBS-A. In other embodiments, the subtype is Unsubtyped-IBS (IBS-U). In still further embodiments, the methods are preferentially useful for treating IBS-D and IBS-A, and are useful for treating IBS-U to a lesser extent.

In further aspects, the methods are useful for treating diarrhea, such as diarrhea caused by viral infections, parasites, bacterial toxins, medications, artificial sweeteners, surgery, and other digestive disorders.

The methods are useful for treating humans, and particularly, are useful for treating both females and males.

In one aspect, the invention provides a method for treating IBS-D, IBS-A or IBS-U, comprising administering a therapeutically effective amount of a pharmaceutical composition comprising a selective opiate receptor modulator, a peripherally selective opiate receptor modulator, a peripherally selective kappa-opiate receptor modulator, a peripherally selective kappa-opiate receptor agonist, and/or a pharmacologically acceptable salt thereof, to a subject having IBS-D, IBS-A, or IBS-U.

In another aspect, the invention encompasses a method of treating at least one symptom of IBS-D, IBS-A, or IBS-U comprising administering to said subject a therapeutically effective amount of a pharmaceutical composition comprising a selective opiate receptor modulator, a peripherally selective opiate receptor modulator, a peripherally selective kappa-opiate receptor modulator, a peripherally selective kappa-opiate receptor agonist, and/or a pharmacologically acceptable salt thereof. The symptoms are selected from the group consisting of: abnormal stool frequency, abnormal stool form, abnormal stool passage, passage of mucus, feeling of a sense of urgency, feeling of abdominal distension, pain, discomfort, and combinations thereof. It is contemplated that said administration ameliorates pain and/or discomfort caused by the disease. In another aspect, said administration normalizes bowel motility.

In one aspect, the pharmaceutical composition comprises N-methyl-N-[(1S)-1-phenyl-2-((3S)-3-hydroxypyrrolidin-1-yl)ethyl]-2,2-diphenylacetamide, a pharmaceutical derivative thereof, and/or a pharmacologically acceptable salt thereof. In one embodiment, the composition comprises N-methyl-N-[(1S)-1-phenyl-2-((3S)-3-hydroxypyrrolidin-1-yl)ethyl]-2,2-diphenylacetamide hydrochloride or asimadoline.

Thus, in one embodiment, the present invention provides a method for treating IBS-D, IBS-A, or IBS-U, comprising administering a therapeutically effective amount of a pharmaceutical composition comprising N-methyl-N-[(1S)-1-phenyl-2-((3S)-3-hydroxypyrrolidin-1-yl)ethyl]-2,2-diphenylacetamide or a pharmacologically acceptable salt thereof to a subject having IBS-D, IBS-A, or IBS-U.

In another embodiment, the invention encompasses a method of treating at least one symptom of IBS-D, IBS-A, or IBS-U comprising administering to said subject a therapeutically effective amount of a pharmaceutical composition comprising N-methyl-N-[(1S)-1-phenyl-2-((3S)-3-hydroxypyrrolidin-1-yl)ethyl]-2,2-diphenylacetamide or a pharmaceutically acceptable salt thereof. The symptoms are selected from the group consisting of: abnormal stool frequency, abnormal stool form, abnormal stool passage, passage of mucus, feeling of abdominal distension, pain, discomfort, and combinations thereof. It is contemplated that said administration ameliorates pain and/or discomfort caused by the disease. In another aspect, said administration normalizes bowel motility.

In a further embodiment, the invention encompasses a method of treating a subject with diarrhea comprising administering to said subject a therapeutically effective amount of a pharmaceutical composition comprising a selective opiate receptor modulator, a peripherally selective opiate receptor modulator, a peripherally selective kappa-opiate receptor modulator, a peripherally selective kappa-opiate receptor agonist, N-methyl-N-[(1S)-1-phenyl-2-((3S)-3-hydroxypyrrolidin-1-yl)ethyl]-2,2-diphenylacetamide and/or a pharmacologically acceptable salt thereof. In one embodiment, the composition comprises N-methyl-N-[(1S)-1-phenyl-2-((3S)-3-hydroxypyrrolidin-1-yl)ethyl]-2,2-diphenylacetamide hydrochloride or asimadoline.

Also encompassed by the invention are kits comprising an effective amount of a pharmaceutical composition comprising a selective opiate receptor modulator, a peripherally selective opiate receptor modulator, a peripherally selective kappa-opiate receptor modulator, a peripherally selective kappa-opiate receptor agonist, N-methyl-N-[(1S)-1-phenyl-2-((3S)-3-hydroxypyrrolidin-1-yl)ethyl]-2,2-diphenylacetamide and/or a pharmacologically acceptable salt thereof and an instruction means for administering said compound to a subject having diarrhea or a subtype of IBS. For example, the subtype can be IBS-A, IBS-D, or IBS-U. In one aspect, the pharmaceutical composition comprises N-methyl-N-[(1S)-1-phenyl-2-((3S)-3-hydroxypyrrolidin-1-yl)ethyl]-2,2-diphenylacetamide hydrochloride.

BRIEF DESCRIPTION OF THE DRAWINGS

FIGS. 1A and B depict the change in pain from baseline by visual analog scale (VAS) (A) and the proportion of days with adequate relief (B) for the IBS-A, IBS-C and IBS-D subtypes. These figures support reduction in pain in IBS-A patients receiving on-demand treatment with asimadoline.

FIGS. 3A and B depict the proportion of months with adequate relief of pain or discomfort associated with IBS in IBS subjects with initial pain scores ≥2.0. FIG. 3A shows results from all IBS subjects, and FIG. 3B shows results from subjects with IBS-D. These figures demonstrate a statistically significant improvement in subjects treated with 0.5 mg and 1.0 mg asimadoline.

FIG. 5A demonstrates that a statistically significant effect of 0.5 mg asimadoline treatment relative to placebo was observed throughout most of the 12 weeks of the trial, starting at week 2.

FIG. 6-1A depicts a comparison between the proportion of months with adequate relief of IBS pain or discomfort in all IBS-D subjects with pain scores ≥2.0 and that in female IBS-D subjects. The graph demonstrates that treatment with 0.5 mg asimadoline produced highly similar results in female and male IBS-D subjects. FIG. 6-2B depicts the proportion of pain-free days in all IBS-D subjects with pain scores ≥2.0. The graph demonstrates that a clinically meaningful benefit was seen as early as week 2, with significance achieved by week 3 and sustained through the duration of treatment. FIG. 6-3C depicts the percent of pain-free days during weeks 1-12 of the clinical trial for all IBS-D subjects with pain scores ≥2.0. Overall, IBS-D patients given 0.5 mg of asimadoline had 21 more pain free days over the 3 month study as compared to patients receiving placebo.

FIG. 7A shows results from IBS-A subjects.

FIGS. 8-1A, 8-1B and 8-2C depict changes in pain scores in IBS-D (A, B) and IBS-A (C) subjects with baseline pain scores ≥2.0. FIGS. 8-1A and 8-1B demonstrate a statistically significant improvement in the pain scores every week (starting at week 3) and every month in IBS-D subjects receiving 0.5 mg asimadoline. Similarly, FIGS. 8-1A and 8-1B demonstrate a statistically significant improvement in the pain scores every month in IBS-D subjects receiving 1.0 mg asimadoline. FIG. 8-2C shows that no statistically significant improvement in the pain scores was observed in IBS-A subjects at these dosages.

FIG. 9A demonstrates a statistically significant increase in the percentage of IBS-D monthly responders with baseline pain scores ≥2.0 treated with 0.5 mg asimadoline in all three months of treatment. In contrast.

FIG. 10A shows statistically significant improvements in overall IBS symptoms in IBS-D subjects treated with 0.5 mg or 1.0 mg asimadoline. Similarly, FIG. 10B demonstrates a statistically significant improvement in overall IBS symptoms in IBS-A subjects treated with 1.0 mg asimadoline.

FIG. 11A shows a statistically significant decrease in daily stool frequency in IBS-D subjects treated with 0.5 mg asimadoline in the second and third months of treatment.

FIGS. 14A and B depict monthly changes in stool consistency, measured using the Bristol scale, in IBS-D and IBS-C subjects with baseline pain scores ≥2.0. Although no statistically significant effect was observed at any of the dosages, asimadoline appeared to soften the stool of IBS-C subjects and harden the stool of IBS-D subjects, thereby normalizing stool consistency.

DETAILED DESCRIPTION OF THE INVENTION

Figure 1:
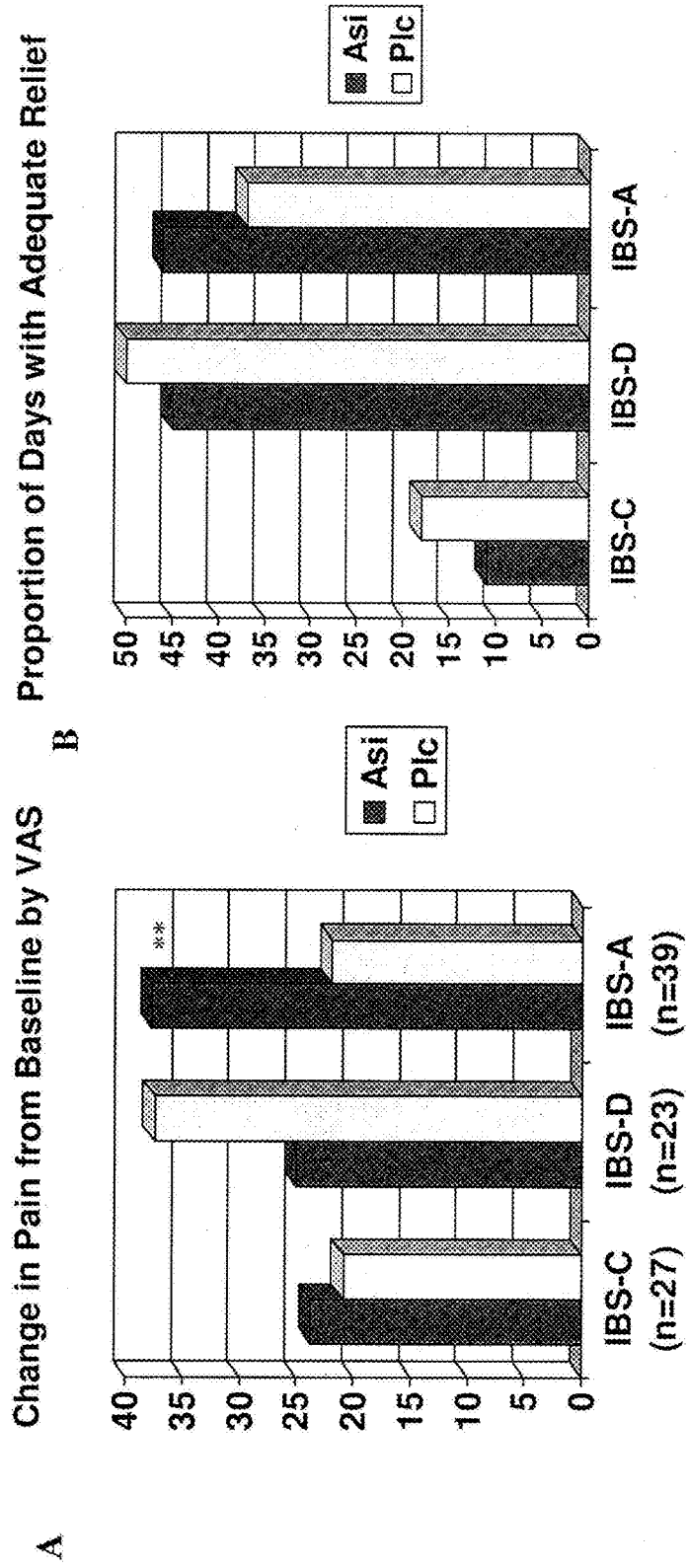

Unless otherwise noted, the terms used herein are to be understood according to conventional usage by those of ordinary skill in the relevant art.

The present invention provides compositions and methods useful in treating one or more subtypes of IBS.

Rome III set out diagnostic criteria for IBS. The Rome III criteria can be found on the interne, at romecriteria.org and in Longstreth et al., (2006) *Gastroenterology*, 130(5), 1480-1491. According to these criteria, a patient is diagnosed with IBS when they have had recurrent abdominal pain or discomfort 3 or more days per month over the preceding 3 months, and the symptoms started 6 or more months ago. The pain/discomfort must also be associated with 2 or more of the following: (1) an improvement with defecation; (2) a change in stool frequency, or (3) a change in stool form. Symptoms that support the diagnosis but that are not part of the diagnostic criteria include abnormal stool frequency, abnormal stool form, defecation straining, urgency, a feeling of incomplete bowel movement, passing mucus, and bloating. (See Longstreth et al., (2006) *Gastroenterology*, 130(5), 1480-1491 for review).

The subtypes of IBS are defined using the Rome III criteria. Rome III classified IBS as having four subtypes: IBS-D, IBS-C, IBS-A, and IBS-U. IBS-C is defined as having hard/lumpy stools (Bristol stool scale 1-2) greater than 25% of the time with loose/mushy/watery stools (Bristol Stool Scale 6-7) less than 25% of the time. IBS-D is defined as having loose/mushy/watery stool (Bristol Stool Scale 6-7) greater than 25% of the time with hard/lumpy stool (Bristol Stool Scale 1-2) less than 25% of the time. IBS-A (also called mixed IBS (IBS-M) is defined as having hard/lumpy stools (Bristol stool scale 1-2) greater than 25% of the time and having loose/mushy/watery stool (Bristol Stool Scale 6-7) greater than 25% of the time. IBS-U is unsubtyped IBS, where there is insufficient abnormality of stool consistency to meet the criteria for IBS-C, IBS-D, or IBS-A. In North America, cases are divided about equally between IBS-C, IBS-D, and IBS-A (Olden (2003) *Cleveland Clinic J. Med.*, 70(Supp 2), S3-S7).

The compounds and methods described herein are useful for treating one or more subtypes of IBS. In one embodiment, the subtype is IBS-D. In another embodiment, the subtype is IBS-A. In other embodiments, the subtype is IBS-U. In still further embodiments, the methods are preferentially useful for treating IBS-D and IBS-A, and are useful for treating IBS-U to a lesser extent. The methods are useful for treating humans, and are useful for treating males and females.

The invention therefore relates to the use of selective opiate receptor modulators, selective opiate receptor modulators; peripherally selective kappa-opiate receptor modulators, and peripherally selective kappa-opiate receptor agonists, and/or pharmacologically acceptable salts thereof for the preparation of medicaments for the treatment of one or more IBS subtypes, and particularly for the treatment of IBS-D and IBS-A.

The invention therefore also relates to the use of N-methyl-N-[(1S)-1-phenyl-2-((3S)-3-hydroxypyrrolidin-1-yl)ethyl]-2,2-diphenylacetamide and/or a pharmacologically acceptable salt thereof for the preparation of medicaments for the treatment of one or more IBS subtypes, and particularly for the treatment of IBS-D and IBS-A.

The active ingredient N-methyl-N-[(1S)-1-phenyl-2-((3S)-3-hydroxypyrrolidin-1-yl)ethyl]-2,2-diphenylacetamide, pharmacologically acceptable salts thereof and processes for its preparation are described in U.S. Pat. Nos. 5,532,266, 6,344,566, and 6,060,504, and in Barber et al. (B. J. Pharmacol. (1994), 113, 1317-1327). N-methyl-N-[(1S)-1-phenyl-2-((3S)-3-hydroxypyrrolidin-1-yl)ethyl]-2,2-diphenylacetamide hydrochloride is commonly referred to as asimadoline.

N-methyl-N-[(1S)-1-phenyl-2-((3S)-3-hydroxypyrrolidin-1-yl)ethyl]-2,2-diphenylacetamide and its salts, including its hydrochloride salt, have an analgesic, anti-inflammatory, antiasthmatic, diuretic, anticonvulsive, neuroprotective and antitussive action and, as a kappa-opiate agonist, is particularly suitable for the treatment of hyperalgesia caused by inflammation, for the treatment of cerebral edema, in undersupply states (hypoxia), pain states, and for ameliorating secondary damage from ischaemia.

The use of N-methyl-N-[(1S)-1-phenyl-2-((3S)-3-hydroxypyrrolidin-1-yl)ethyl]-2,2-diphenylacetamide or pharmacologically acceptable salts thereof for the preparation of a medicament for the treatment of inflammatory intestinal diseases and the disease symptoms associated therewith, for the treatment of severe pain, in particular of pain hypersensitivity occurring in back complaints, burn injuries, sunburn and rheumatic diseases, and for the treatment of postoperative pain and the ileus which frequently occurs after abdominal operations, are disclosed in EP 0 752 246 and U.S. Pat. No. 5,776,972.

Additionally, it was previously suggested that N-methyl-N-[(1S)-1-phenyl-2-((3S)-3-hydroxypyrrolidin-1-yl)ethyl]-2,2-diphenylacetamide and/or a pharmacologically acceptable salt thereof may be suitable for the treatment of functional gastrointestinal diseases associated with pain and/or increased or reduced peristalsis (See U.S. patent application Ser. No. 10/514,887, and Barber & Gottschlich (1997) Expert Opin. Invest. Drugs, 6(10), 1351-1368). Such diseases include IBS, non-ulcerative functional dyspepsia, obstipation, in particular opiate-induced obstipation. It has also been suggested that asimadoline may be useful for the treatment of arthritis, migraines, psoriasis or other itching skin diseases, dysmenorrhea and fibromyalgia (See U.S. Patent Publication No. 20040157913).

Asimadoline has a number of attractive pharmacokinetic and pharmacodynamic characteristics as a therapeutic agent, including high bioavailability (50%), rapid onset, poor penetration of the blood-brain barrier, high affinity for the kappa-opiate receptor ($IC_{50}$ 1.2 nM), and high selectivity for the kappa-opiate receptor (the ratio of asimadoline $IC_{50}$ values for kappa, mu and delta opiate receptors is about 1:501:498, respectively), and a half-life of about 2-3 hours. Bioavailability was determined in fasting subjects, however, food interaction studies showed that eating does not substantially impact bioavailability.

In one aspect, the invention encompasses a method of treating at least one symptom of a subtypes of IBS, such as IBS-D, IBS-A, or IBS-U, comprising administering to said subject a therapeutically effective amount of a pharmaceutical composition comprising a selective opiate receptor modulator, a peripherally selective opiate receptor modulator, a peripherally selective kappa-opiate receptor modulator, a peripherally selective kappa-opiate receptor agonist, N-methyl-N-[(1S)-1-phenyl-2-((3S)-3-hydroxypyrrolidin-1-yl)ethyl]-2,2-diphenylacetamide and/or a pharmacologically acceptable salt thereof. The symptoms are selected from the group consisting of: abnormal stool frequency, abnormal stool form, abnormal stool passage, passage of mucus, feeling of abdominal distension, pain, discomfort, and combinations thereof. It is contemplated that said administration ameliorates pain and/or discomfort caused by the disease. In another aspect, said administration normalizes bowel motility.

In further aspects, selective opiate receptor modulators, selective opiate receptor modulators, peripherally selective kappa-opiate receptor modulators, peripherally selective kappa-opiate receptor agonists, N-methyl-N-[(1S)-1-phenyl-2-((3S)-3-hydroxypyrrolidin-1-yl)ethyl]-2,2-diphenylacetamide and/or pharmacologically acceptable salts thereof are useful for treating diarrhea. They are useful for treating diarrhea caused by viral infections (i.e., HIV, Norwalk virus, cytomegalovirus, viral hepatitis, herpes simplex virus, and rotavirus), parasites (i.e., Giardia lamblia, and cryptosporidium), bacteria (i.e., campylobacter, salmonella, shigella, E. coli), medications (i.e., antibiotics), artificial sweeteners (i.e., sorbitol and mannitol), surgery, radiation therapy, cancer, diabetes, hyperthyroidism, and other digestive disorders (i.e., Crohn's disease, celiac disease and ulcerative colitis). These are non-limiting examples of the causes of diarrhea, and it is contemplated that the compounds discussed herein may be useful in treating diarrhea regardless of the cause.

In further aspects, selective opiate receptor modulators, selective opiate receptor modulators, peripherally selective kappa-opiate receptor modulators, peripherally selective kappa-opiate receptor agonists, N-methyl-N-[(1S)-1-phenyl-2-((3S)-3-hydroxypyrrolidin-1-yl)ethyl]-2,2-diphenylacetamide and/or pharmacologically acceptable salts thereof for the preparation of medicaments for the treatment of diarrhea.

A compound is deemed to be suitable as a selective opiate receptor modulator for use according to the invention if it shows an affinity to one or more opiate receptors, preferably to the mu- and kappa-opiate receptors, more preferably to the mu- or the kappa-opiate receptors, and especially to the kappa-opiate receptor that lies, determined as $IC_{50}$-value, in the range of about 0.01 nmol to about 100 in the range of about 0.05 nmol to about 10 µmol, in the range of about 0.1 nmol to about 3 µmol, in the range of about 0.5 nmol to 1 µmol, or in the nanomolar range. In certain aspects, the affinity to the kappa opiate receptor, determined as $IC_{50}$-value, is about 0.01 nM, 0.05 nM, 0.1 nM, 0.2 nM, 0.3 nM, 0.4 nM, 0.5 nM, 0.6 nM, 0.7 nM, 0.8 nM, 0.9 nM, 1 nM, 1.2 nM, 1.5 nM, 1.7 nM, 2 nM, 3, nM, 4 nM, 5 nM, 10 nM or higher.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

A compound is suitable for use according to the invention if it has a pharmaceutical half-life of in the range of about 1-10 hours, in the range of about 1-8 hours, in the range of about 1-6 hours, in the range of about 1-4 hours, or in the range of about 2-3 hours.

A compound is considered to be suitable for use according to the invention if it is peripherally selective, i.e., shows poor penetration of the blood-brain barrier. A peripherally selective compound according to the invention means a compound that shows high selectivity for the peripheral nervous system of the patient when administered to said patient. Peripherally selective compounds preferably show little or no detectable impact on the central nervous system of the patient upon administration to said patient at dosage levels that exert a therapeutic effect on the peripheral nervous system.

A compound is deemed to be suitable for use according to the invention if the ratio of its affinity for the kappa-opiate receptor, determined as $IC_{50}$-value, to its affinity for another opiate receptor subtype, determined as $IC_{50}$-value, lies in the range of about 1:100 to 1:2000, in the range of about 1:200 to 1:1500, in the range of about 1:300 to 1:1200, in the range of about 1:400 to 1:1000, or having a ratio of about 1:100, 1:200, 1:300, 1:400, 1:500, 1:600, 1:700, 1:800, 1:900, 1:1000 or less.

A compound is considered to be suitable for use according to the invention if it shows a bioavailability in a human subject of greater than or equal to about 10%, 20%, 30%, 40%, 50%, 60%, or 70%.

In one aspect, as described above, the compound used in the methods of the invention is N-methyl-N-[(1S)-1-phenyl-2-((3S)-3-hydroxypyrrolidin-1-yl)ethyl]-2,2-diphenylacetamide, and/or a pharmacologically acceptable salt thereof. Also contemplated are the use of pharmaceutical derivatives thereof, such as those described in U.S. Patent Publication No. 20060122255.

Other modulating compounds for use according to the invention are selected from a group consisting of Alvimopan (see, for example, *Am. J. Surg.* 2001 November; 182 (5ASuppl): 27S-38S), Loperamide (see, for example, *J. Pharmacol. Exp. Ther.* 1999 April; 289 (1): 494-502), Spiradoline (see, for example, *Pol. J. Pharmacol.* 1994 January-April; 46 (1-2): 37-41), Fedotozine (see, for example, *Expert Opin. Investig. Drugs* 2001 January; 10(1): 97-110), Pentazocine (see, for example, *Biol. Pharm. Bull.* 1997 November; 20(11): 1193-8), Enadoline (*Psychopharmacology* 2001 September; 157(2):151-62), IC1204448 (see, for example, *Br. J. Pharmacol.* 1992 August; 106(4): 783-9), U-50488H (see, for example, *Life Sci.* 2002 Mar. 1; 70(15): 1727-40), FE 200665 and FE 200666 (Rivière et al., 1999 *Acta. Neurobiol. Exp.* 59:186; Binder et al., 2001 *Anesthesiology* 94: 1034-1044), TRK-820 (see, for example, *Life Sci.* 1999; 65(16): 1685-94), ADL 10-0101 (see, for example, *Pain* 2002 March; 96(1-2): 13-22), ADL 10-0116 (see, for example, *Pain* 2002 March; 96 (1-2): 13-22), ADL 1-0398 (from Adolor Corp., USA), U 69,593 (see, for example, *J. Neurosci.*, 2000 August; 20(15):5874-5879), EMD 60400 (*Chirality* 6: 685-689, 1994), Salvinorin A (*Life Sciences* 75:2615-2619, 2004), CR665 and CR666 (both from Cara Therapeutics Inc.).

In one aspect of the invention, the modulating compounds are selected from the group consisting of N-methyl-N-[(1S)-1-phenyl-2-((3S)-3-hydroxypyrrolidin-1-yl)ethyl]-2,2-diphenylacetamide, ICI1204448, U-50488H, ADL 10-0101, ADL 10-0116, ADL 1-0398, FE 200665, FE 200666, EMD 60400, U 69,593, CR665, CR666, derivatives, combinations and pharmaceutically acceptable salts thereof.

Thus, in one embodiment, the present invention provides a method for treating IBS-D, comprising administering a therapeutically effective amount of a pharmaceutical composition comprising N-methyl-N-[(1S)-1-phenyl-2-((3S)-3-hydroxypyrrolidin-1-yl)ethyl]-2,2-diphenylacetamide and/or a pharmacologically acceptable salt thereof to a subject having IBS-D. In another aspect, the invention provides a method for treating IBS-A, comprising administering a therapeutically effective amount of a pharmaceutical composition comprising N-methyl-N-[(1S)-1-phenyl-2-((3S)-3-hydroxypyrrolidin-1-yl)ethyl]-2,2-diphenylacetamide or a pharmacologically acceptable salt thereof to a subject having IBS-A. In still another aspect, the invention provides treating a patient with IBS-U with a therapeutically effective amount of a pharmaceutical composition comprising N-methyl-N-[(1S)-1-phenyl-2-((3S)-3-hydroxypyrrolidin-1-yl)ethyl]-2,2-diphenylacetamide or a pharmacologically acceptable salt thereof.

In another embodiment, the invention encompasses a method of treating at least one symptom of IBS-D, IBS-A, or IBS-U comprising administering to said subject a therapeutically effective amount of a pharmaceutical composition comprising N-methyl-N-[(1S)-1-phenyl-2-((3S)-3-hydroxypyrrolidin-1-yl)ethyl]-2,2-diphenylacetamide and/or a pharmaceutically acceptable salt thereof. The symptoms are selected from the group consisting of: abnormal stool frequency, abnormal stool form, abnormal stool passage, passage of mucus, feeling of abdominal distension, pain, discomfort, and combinations thereof. It is contemplated that said administration ameliorates pain and/or discomfort caused by the disease. In another aspect, said administration normalizes bowel motility.

In one embodiment, the pharmaceutical composition comprises N-methyl-N-[(1S)-1-phenyl-2-((3S)-3-hydroxypyrrolidin-1-yl)ethyl]-2,2-diphenylacetamide hydrochloride.

In another embodiment, the individual is diagnosed with the IBS subtype prior to administration with the pharmaceutical composition. For example, the individual is diagnosed with IBS-D, IBS-A, or IBS-U prior to administering the pharmaceutical composition. In one aspect, the pharmaceutical composition is not administered to an individual after diagnosis with IBS-C.

Pharmaceutical compositions may be administered by oral, parenteral (e.g., intramuscular, intraperitoneal, intravenous, intracisternal injection or infusion, subcutaneous injection, or implant), inhalation spray, nasal, vaginal, rectal, sublingual, or topical routes of administration. The pharmaceutical compositions may be formulated in suitable dosage unit formulations appropriate for each route of administration.

It is not intended that the present invention be limited to particular formulations or particular modes of administration. In one embodiment, the composition is formulated for oral, parenteral, intranasal, topical, or injectable administration. Non-limiting examples of injectable administration are intracavernous injection, subcutaneous injection, intravenous injection, intramuscular injection and intradermal injection. The pharmaceutical composition can be formulated for oral administration in a dosage ranging from about 0.1 mg-25 mg per day. The pharmaceutical composition can also be formulated for injectable administration in a dosage ranging from about 0.1 mg-25 mg per day. In other embodiments, the dosage ranges from about 0.1 mg to about 10 mg per day. In preferred embodiments, the dose ranges from about 0.3 mg to about 2.0 mg per day.

According to still further features in the described embodiments, administering is effected from about 1 to about 4 times per day. In one aspect, administration is twice per day. In a further aspect, said administration is effected according to the development of symptoms of IBS in the subject. For example, administration may be p.r.n., or as needed, depending upon the symptoms in the subject.

In one aspect, the subject with IBS-D is administered about 1 mg or about 2 mg per day. In other aspects, the subject with IBS-D has been diagnosed with moderate or severe pain. In one aspect, moderate or severe pain is diagnosed based upon self-reporting of degree of pain.

In another aspect, the subject with IBS-A is administered about 1 mg or about 2 mg per day. In other aspects, the subject with IBS-A has been diagnosed with moderate or severe pain.

Pharmaceutical compositions of the present invention can be formulated in a solid or liquid dosage form. For example, the pharmaceutical compositions may be formulated as a solid in the form of tablets, capsules, granules, powders, and similar compounds. The pharmaceutical compositions may also be formulated as a liquid in the form of syrups, injection mixtures, and the like.

The pharmaceutical composition may be taken with or without food. If taken without food, it may be taken before or after a meal.

Also encompassed by the invention are kits comprising an effective amount of a pharmaceutical composition comprising a selective opiate receptor modulator, preferably a peripherally selective opiate receptor modulator, more preferably a peripherally selective kappa-opiate receptor modulator, and especially a peripherally selective kappa-opiate receptor agonist, or a pharmacologically acceptable salt thereof and an instruction means for administering said compound to a subject having a subtype of IBS. For example, the subtype can be IBS-A, IBS-D, or IBS-U.

Further encompassed by the invention are kits comprising an effective amount of a pharmaceutical composition comprising N-methyl-N-[(1S)-1-phenyl-2-((3S)-3-hydroxypyrrolidin-1-yl)ethyl]-2,2-diphenylacetamide or a pharmaceutically acceptable salt thereof and an instruction means for administering said compound to a subject having a subtype of IBS. For example, the subtype can be IBS-A, IBS-D, or IBS-U. In one aspect, the pharmaceutical composition comprises N-methyl-N-[(1S)-1-phenyl-2-((3S)-3-hydroxypyrrolidin-1-yl)ethyl]-2,2-diphenylacetamide hydrochloride.

The present invention may be understood more readily by reference to the following detailed description of the preferred embodiments of the invention and the Examples included herein. All patents, patent applications, published applications, websites and other publications referred to herein, as well as references cited within those publications, are incorporated by reference in their entirety. In the event that there are a plurality of definitions for terms herein, those in this section prevail.

However, before the present compounds, compositions, and methods are disclosed and described, it is to be understood that this invention is not limited to specific salts, specific IBS subtypes, specific symptoms, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

A. DEFINITIONS

As used herein, the singular form "a", "an", and "the" includes plural references unless indicated otherwise. For example, reference to "an active agent" or "a pharmacologically active agent" includes a single active agent as well as two or more different active agents in combination, reference to "a pharmacologically acceptable salt" includes one or more different salts as well as a single salt, reference to "a carrier" includes mixtures of two or more carriers as well as a single carrier, and the like.

As used herein, the term "subject," "individual," or "patient," used interchangeably, refers to any animal, including mammals, preferably mice, rats, other rodents, rabbits, dogs, cats, swine, cattle, sheep, horses, or primates, and most preferably humans. In another embodiment, a subject is a human subject. In other embodiments, the human subject is a female or a male.

A "peripherally selective" compound according to the invention preferably means a compound that shows little, or more preferably, no detectable impact on the central nervous system of the patient upon administration to said patient.

As used herein, the term "active agent" refers to N-methyl-N-[(1S)-1-phenyl-2-((3S)-3-hydroxypyrrolidin-1-yl)ethyl]-2,2-diphenylacetamide, salts, solvates, prodrugs, and/or derivatives thereof.

The compound N-methyl-N-[(1S)-1-phenyl-2-((3S)-3-hydroxypyrrolidin-1-yl)ethyl]-2,2-diphenylacetamide is known, and has been described, for example, in EP-A-0 569 802 (U.S. Pat. No. 5,532,226), EP-A-0 752 246 (U.S. Pat. No. 5,776,972 and U.S. Pat. No. 5,977,161), DE-A-198 49 650, EP-A-0 761 650 (U.S. Pat. No. 6,060,504) and EP-A-1 073 634 (U.S. Pat. No. 6,344,566).

Asimadoline is an active substance of the diarylacetamide kappa opiates. Its chemical designation is N-[(1S)-2-[(3S)-3-hydroxypyrrolidin-1-yl]-1-phenylethyl]-N-methyl-2,2-diphenylacetamide, hydrochloride, and its empirical formula is $C_{27}H_{30}N_2O_2 \times HCl$. The molecular weight is 451.01, and the structural formula is:

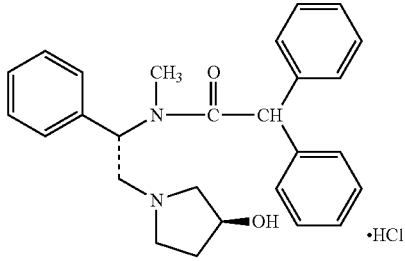 [SMILES: CN(C(=O)C(c1ccccc1)c1ccccc1)[C@H](CN1CC[C@H](O)C1)c1ccccc1 ; Cl]

Asimadoline is a white powder which has a solubility in water of 11.6 g/L and a solubility in ethanol of 5.4 g/L. The substance is slightly sensitive to moisture, but stable against heat, aerial oxygen and light. It is not hygroscopic.

The term "N-methyl-N-[(1S)-1-phenyl-2-((3S)-3-hydroxypyrrolidin-1-yl)ethyl]-2,2-diphenylacetamide" encompasses the salts, solvates, prodrugs, and derivatives of the compound. For example, it includes the derivatives described in U.S. Patent Publication No. 20060122255. The invention also relates to the optically active forms (stereoisomers), preferably the enantiomers, the racemates and the diastereomers, and the hydrates and solvates of N-methyl-N-[(1S)-1-phenyl-2-((3S)-3-hydroxypyrrolidin-1-yl)ethyl]-2,2-diphenylacetamide. The term "solvates" according to the invention is taken to mean adductions of inert solvent molecules onto N-methyl-N-[(1S)-1-phenyl-2-((3S)-3-hydroxypyrrolidin-1-yl) ethyl]-2,2-diphenylacetamide owing to their mutual attractive force. Solvates include, for example, mono- or dihydrates or alcoholates. "Prodrugs" refers to compounds that have been modified by means of additional groups or that contain additional groups, such as, but not limited to, alkyl or acyl groups, sugars or oligopeptides that are rapidly cleaved in the organism to give the active agent.

As used herein, the term "bioavailability" is a measurement of the extent of a therapeutically active drug that reaches the systemic circulation and is available at the site of action.

As used herein, the terms "pharmaceutically acceptable salts" or "pharmaceutically acceptable derivatives" of the compounds of the present invention encompass any salts or esters that may be readily prepared by those of skill in this art. Pharmaceutically acceptable salts of the compounds of this invention include, for example, those derived from pharmaceutically acceptable inorganic and organic acids and bases. Salts derived from appropriate bases include, but are not limited to, alkali metal (e.g., sodium), alkaline earth metal (e.g., magnesium), ammonium and $N(C_{1-4}\ alkyl)_4^+$ salts. Examples of suitable acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic, and benzenesulfonic acids. Other acids, such as oxalic, while not in themselves pharmaceutically acceptable, may be employed in the preparation of salts useful as intermediates in obtaining the compounds of the invention and their pharmaceutically acceptable acid salts. In one aspect of the invention, the pharmacologically acceptable salt is. N-methyl-N-[(1S)-1-phenyl-2-((3S)-3-hydroxypyrrolidin-1-yl)ethyl]-2,2-diphenylacetamide hydrochloride, also known as EMD 61753 and asimadoline.

As used herein, "to treat" or "therapeutic" and grammatically related terms, refer to any improvement or amelioration of any consequence of disease; full eradication of disease is not required. Amelioration of symptoms of a particular disorder refers to any lessening of symptoms, whether permanent or temporary, that can be attributed to or associated with administration of the composition. In one aspect, the administration of a compound of the invention improves, prevents, or relieves one or more symptoms or clinically observed sequalae for clinically diagnosed disorders as described herein, including functional bowel disorders, such as IBS and one or more IBS subtypes, and diarrhea.

As used herein, the terms "administration" or "administering" a compound refers to any suitable method of providing a compound of the invention of the invention to a subject.

As used herein, "normalizes bowel motility" refers to the ability of the compounds of the invention to alter the motility of the bowel in the treated subject such that the motility is closer to standard or average motility than it was prior to treatment. For example, normalizing bowel motility in subjects with constipation involves increasing the frequency of stool passage and/or reducing the hardness and lumpiness of the stool, while normalizing bowel motility in subjects with diarrhea involves reducing the frequency of stool passage and/or making the stool less watery and mushy.

In one aspect, the invention features methods and compositions for decreasing intestinal motility. Intestinal motility involves spontaneous coordinated dissentions and contractions of the stomach, intestines, colon and rectum to move food through the gastrointestinal tract during the digestive process.

As used herein, "discomfort" refers to an uncomfortable sensation not described as pain.

"Constipation" is used in its conventional sense to mean infrequent or difficult evacuation of feces.

"Diarrhea" is used in its conventional sense to mean a frequent and generally profuse discharge of loose or fluid evacuations from the intestines without straining.

By an "effective" amount or a "therapeutically effective amount" of a drug or pharmacologically active agent is meant a nontoxic but sufficient amount of the drug or agent to provide the desired effect, i.e., relieving the symptoms associated with one or more IBS subtypes, as explained above, or by ameliorating the symptoms of diarrhea. It is recognized that the effective amount of a drug or pharmacologically active agent can vary depending on the route of administration, the selected compound, and the species to which the drug or pharmacologically active agent is administered, as well as the age, weight, and sex of the individual to which the drug or pharmacologically active agent is administered. It is also recognized that one of skill in the art can determine appropriate effective amounts by taking into account such factors as metabolism, bioavailability, and other factors that affect plasma levels of a drug or pharmacologically active agent following administration within the unit dose ranges disclosed further herein for different routes of administration.

By "as-needed" dosing, also known as "pro re nata" "prn" dosing, and "on demand" dosing or administration is meant the administration of a dose of the active agent at a time when suppression of the painful and non-painful symptoms of IBS would be desirable, or whereby suppression of diarrhea would be desirable.

Alternatively, the active agent is administered on a continuous basis, such as daily, multiple times per day (i.e., 2-4 times per day), or on a more or less frequent schedule. Determination of a dosing schedule is well within the capabilities of one of ordinary skill in the art.

As used herein, the phrase "pharmacological half-life" describes the time required for half the quantity of a drug or other substance deposited in a living organism to be metabolized or eliminated from the plasma by normal biological processes. This phrase is also referred to herein interchangeable as "half life".

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert composition that is physiologically compatible with humans or other mammals.

By "pharmaceutically acceptable formulation" or "pharmaceutical composition" it is meant a composition or formulation that allows for the effective distribution of the compounds of the invention in that physical location most suitable for their desired activity.

By "systemic administration" is meant in vivo systemic absorption or accumulation of a compound in the blood stream followed by distribution throughout the entire body.

B. DISEASE TREATMENT

The invention provides compositions and methods to treat a subject with IBS, and particularly, to treat one or more subtypes of IBS. In one embodiment, the subtype is IBS-A. In another embodiment, the subtype is IBS-D. In other embodiments, the subtype is IBS-U. In still further embodiments, the methods are particularly useful for treating IBS-D and IBS-A, and are useful for treating IBS-U to a lesser extent.

The invention further provides compositions and methods to treat a subject with diarrhea.

The methods are useful for treating humans, and particularly, are useful for treating both males and females.

Single or multiple administration of the active agent can be given using any convenient mode of administration, including but not limited to oral, intravenous, intraperitoneal, subcutaneous, and intradermal.

Exemplary formulations include, but are not limited to, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. The dosage of the compounds of the invention will vary according to the extent and severity of the need for treatment, the activity of the administered composition, the general health of the subject, and other considerations well known to the skilled artisan.

C. PHARMACEUTICAL COMPOSITIONS

The compounds of the invention as described herein can be incorporated into pharmaceutical compositions suitable for administration. Such compositions typically comprise the agent and a pharmaceutically acceptable carrier. Supplementary active compounds can also be incorporated into the compositions.

Various pharmaceutical compositions and techniques for their preparation and use will be known to those of skill in the art in light of the present disclosure. For a detailed listing of suitable pharmacological compositions and associated administrative techniques one may refer to the detailed teachings herein, which may be further supplemented by texts such as Remington: The Science and Practice of Pharmacy 20th Ed. (Lippincott, Williams & Wilkins 2003).

Suitable compositions and dosage forms include tablets, capsules, caplets, pills, gel caps, troches, dispersions, suspensions, solutions, syrups, transdermal patches, gels, powders, magmas, lozenges, creams, pastes, plasters, lotions, discs, suppositories, liquid sprays for nasal or oral administration, dry powder or aerosolized formulations for inhalation, compositions and formulations for intravesical administration and the like. Further, those of ordinary skill in the art can readily deduce that suitable formulations involving these compositions and dosage forms, including those formulations as described elsewhere herein.

Pharmaceutically-acceptable materials, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Therapeutic formulations can be solubilized and administered via any route capable of delivering the therapeutic composition to the site of treatment in the subject. Potentially effective routes of administration include, but are not limited to, oral, intravenous, parenteral, intraperitoneal, intramuscular, intradermal, intraorgan, orthotopic, and the like. One formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic preparations can be lyophilized and stored as sterile powders, preferably under vacuum, and then reconstituted in bacteriostatic water (containing for example, benzyl alcohol preservative) or in sterile water prior to injection.

The clinical trials described herein used tablets containing 0.15, 0.5 or 1.0 mg of asimadoline and the following inactive ingredients: lactose, cellulose microcrystalline, hypromellose, croscarmellose sodium, magnesium stearate, Macrogol 400, Dimeticon 100, titanium dioxide and iron oxide red. The use of other inactive ingredients is contemplated.

In one aspect, the composition is a sustained-release composition.

Sustained-release forms are often designed to maintain therapeutic drug concentrations for greater than 12 hours. The absorption rate can be controlled by coating drug particles with wax or other water-insoluble material, by embedding the drug in a matrix from which it is released slowly during transit through the GI tract, or by complexing the drug with ion-exchange resins.

Thus, for example, a sustained-release formulation in tablet form, may be based on the use of a hydrophilic polymer which swells in contact with gastrointestinal fluids, to form a gel, which creates a barrier that enrobes the tablet. The barrier limits physical exchanges between the inside of the tablet and the surrounding medium. As a consequence, intrusion of water towards the tablet matrix and diffusion of drug are slowed down, allowing a controlled slow release of the drug.

Various types of polymers may be used as a matrix for the sustained-release of drugs, such as polyvinyl chloride, polyethylene polyamides, ethylcellulose, silicone, poly (hydroxyethyl methacrylate), other acrylic co-polymers, and polyvinylacetate-polyvinyl chloride copolymers.

Thus, a sustained-release formulation for delivery of the opioid modulators of the present invention provides for release over a period that ranges from about 2 hour to about 24 hours, preferably from about 4 hours to about 24 hours and hence, for release over a period of at least 4 hour, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. Alternatively, such a sustained-release formulation provides for release of the opioid modulators over a period of more than 24 hours and up to 48 hours.

D. DOSAGE AND ADMINISTRATION

The concentration of the active agent in any of the aforementioned dosage forms and compositions can vary a great deal, and will depend on a variety of factors, including the type of composition or dosage form, the corresponding mode of administration, the nature and activity of the specific active agent, and the intended drug release profile. Preferred dosage forms contain a unit dose of active agent, i.e., a single therapeutically effective dose. For creams, ointments, etc., a "unit dose" requires an active agent concentration that provides a unit dose in a specified quantity of the formulation to be applied. The unit dose of any particular active agent will depend, of course, on the active agent and on the mode of administration.

For the active agents of the present invention, the unit dose for oral, transmucosal, topical, transdermal, and parenteral administration will be in the range of from about 1 ng to about 1000 mg, about 5 ng to about 950 mg, about 10 ng to about 900 mg, about 20 ng to about 800 mg, about 30 ng to about 750 mg, about 40 ng to about 700 mg, about 50 ng to about 650 mg, about 100 ng to about 600 mg, about 200 ng to about 550 mg, about 250 ng to about 500 mg, about 400 ng to about 450 mg, about 500 ng to about 400 mg, about 1 µg to about 350 mg, about 5 µg to about 300 mg, about 10 µg to about 250 mg, about 20 µg to about 200 mg, about 40 µg to about 175 mg, about 50 µg to about 150 mg, about 75 µg to about 125 mg, about 100 µg to about 100 mg, about 200 µg to about 75 mg, about 300 µg to about 50 mg, about 400 µg to about 25 mg, about 0.5 mg to about 20 mg, about 0.5 mg to about 10 mg, about 0.5 mg to about 5 mg, about 0.1 mg to about 10 mg, about 0.1 mg to about 5 mg, or about 0.3 mg to about 2 mg.

In one aspect, the wherein the pharmaceutical composition is formulated to be administered orally, once or twice daily, in a range from about 0.3 mg to about 2 mg.

A therapeutically effective amount of a particular active agent administered to a given individual will, of course, be dependent on a number of factors, including the concentration of the specific active agent, composition or dosage form, the selected mode of administration, the age and general condition of the individual being treated, the sex of the individual, the severity of the individual's condition, and other factors known to the prescribing physician.

In one aspect, the dosing is short-term, while in other aspects, the dosing is long-term. By "short-term," it is meant that the active agent is administered to the patient for a defined period of time, typically measured in days or weeks. For example, the active agent may be given for the duration of the symptoms for the treatment of diarrhea. In another example, the active agent may be given for a term of 1, 2, 3, 4, 5, 6, or 7 days, or 1, 2, 3, 4, 5, or 6 or more weeks. By "long-term," it is meant that the active agent is administered to the patient for undefined period of time. In one example, the active agent is given to a patient with IBS-A, IBS-D, or IBS-U to treat the disease, and continues to be administered even after one or more symptoms has been ameliorated.

A therapeutically effective amount according to the present invention can include an amount effective to show a reduction in the frequency or intensity of at least one symptom associated with the disease. For example, in a patient with IBS, an effective amount of the active agents of the present invention can be an amount effective at reducing abdominal pain and/or discomfort. A further example of an effective amount of the active agents of the present invention for treating a patient with diarrhea would be an amount effective for reducing the onset or frequency of loose stool in the patient with diarrhea, such as in a patient with IBS-A, IBS-D, IBS-U, or diarrhea unrelated to IBS, or an amount for normalizing the motility of the bowel.

The above therapeutic approaches can be combined with any one of a wide variety of therapeutic regimens for the treatment of IBS or diarrhea. In one embodiment, for example, asimadoline is administered in conjunction with stress management counseling, and/or diet and lifestyle changes. In other aspects, asimadoline is administered in conjunction with the administration of fiber supplements, antidiarrheals, laxatives, anticholinergic agents, antidepressants, alosetron, tegaserod, and/or combinations thereof. It is further contemplated that asimadoline may be co-formulated with fiber supplements, antidiarrheals, laxatives, anticholinergic agents, antidepressants, alosetron, tegaserod, and/or combinations thereof.

E. KITS

In one embodiment, a packaged kit is provided that contains the pharmaceutical formulation to be administered, i.e., a pharmaceutical formulation containing a therapeutically effective amount of a selective opiate receptor modulator, a peripherally selective opiate receptor modulator, a peripherally selective kappa-opiate receptor modulator, a peripherally selective kappa-opiate receptor agonist, N-methyl-N-[(1S)-1-phenyl-2-((3S)-3-hydroxypyrrolidin-1-yl)ethyl]-2,2-diphenylacetamide, and/or one of its pharmacologically acceptable salts, a container, preferably sealed, for housing the formulation during storage and prior to use, and instructions for carrying out drug administration in a manner effective for treating IBS or diarrhea. If the drug is used for diarrhea, the instructions may be specific for treating one or more subtypes of IBS. The instructions will typically be written instructions on a package insert and/or on a label. Depending on the type of formulation and the intended mode of administration, the kit may also include a device for administering the formulation. Formulations may be any suitable formulations as described herein. For example, formulations may be an oral dosage form containing a unit dosage of the selected salt of N-methyl-N-[(1S)-1-phenyl-2-((3S)-3-hydroxypyrrolidin-1-yl)ethyl]-2,2-diphenylacetamide.

The kit may contain multiple formulations of different or the same dosages of the same agent. The kit may also contain multiple formulations of different active agents. The kit may contain formulations suitable for sequential, separate and/or simultaneous use in treating IBS.

The parts of the kit may be independently held in one or more containers—such as bottles, syringes, plates, wells, blister packs, or any other type of pharmaceutical packaging.

Instructions, either as inserts or as labels, indicating quantities of the components to be administered, guidelines for administration, and/or guidelines for mixing the components, can also be included in the kit. The instructions may also indicate typical adverse effects and contraindications, with instructions to discontinue administration should particular side effects occur. The systems affected with treatment using asimadoline may include musculoskeletal, central and peripheral nervous system, psychiatric, gastrointestinal, genitourinary, respiratory, and the body as a whole. Adverse effects may include constipation, diarrhea, headache, nausea, sinusitis, abdominal pain, and dizziness.

F. INSURANCE CLAIMS

In general, the processing of an insurance claim for the coverage of a given medical treatment or drug therapy involves notification of the insurance company, or any other entity, that has issued the insurance policy against which the claim is being filed, that the medical treatment or drug therapy will be performed. A determination is then made as to whether the medical treatment or drug therapy that will be performed is covered under the terms of the policy. If covered, the claim is then processed, which can include payment, reimbursement, or application against a deductible.

The present invention encompasses a method for processing an insurance claim under an insurance policy for a selective opiate receptor modulator, preferably a peripherally selective opiate receptor modulator, more preferably a peripherally selective kappa-opiate receptor modulator, and especially a peripherally selective kappa-opiate receptor agonist, or one of its pharmacologically acceptable salts used in the treatment of IBS, and more particularly, in the treatment of an IBS subtype. This method comprises: 1) receiving notification that treatment using said a selective opiate receptor modulator, a peripherally selective opiate receptor modulator, a peripherally selective kappa-opiate receptor modulator, a peripherally selective kappa-opiate receptor agonist, N-methyl-N-[(1S)-1-phenyl-2-((3S)-3-hydroxypyrrolidin-1-yl) ethyl]-2,2-diphenylacetamide, and/or a pharmacologically acceptable salt thereof will be performed or notification of a prescription; 2) determining whether said treatment using said selective opiate receptor modulator, peripherally selective opiate receptor modulator, peripherally selective kappa-opiate receptor modulator, peripherally selective kappa-opiate receptor agonist, N-methyl-N-[(1S)-1-phenyl-2-((3S)-3-hydroxypyrrolidin-1-yl)ethyl]-2,2-diphenylacetamide, and/or a pharmacologically acceptable salt thereof is covered under said insurance policy; and 3) processing said claim for treatment of IBS using said a selective opiate receptor modulator, a peripherally selective opiate receptor modulator, a peripherally selective kappa-opiate receptor modulator, a peripherally selective kappa-opiate receptor agonist, N-methyl-N-[(1S)-1-phenyl-2-((3S)-3-hydroxypyrrolidin-1-yl) ethyl]-2,2-diphenylacetamide, and/or a pharmacologically acceptable salt thereof, including payment, reimbursement, or application against a deductible. This method encompasses the processing of claims for using asimadoline for the treatment of IBS-A, IBS-D, and IBS-U.

The following examples are not intended to limit the scope of the claims to the invention, but are rather intended to be exemplary of certain embodiments. Any variations in the exemplified methods that occur to the skilled artisan are intended to fall within the scope of the present invention. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

EXAMPLES

Example 1

On-Demand Administration of Asimadoline is Useful for Treating IBS-A

A randomized, parallel group, double-blind, placebo controlled study evaluating the effects of a flexible dose of asimadoline (0.5 mg p.r.n. up to 1.0 mg q.i.d. for four weeks) or identical appearing placebo on improvement of pain and gastrointestinal symptoms in participants with IBS was performed.

Study Population

A total of 155 patients with IBS were recruited. Inclusion criteria included non-pregnant, non breast-feeding females between the ages of 18 and 65; diagnosis of IBS by Rome II criteria; absence of alarm symptoms; acceptable method of contraception; and abdominal pain or discomfort of at least 40 mm on a 100 mm visual analog scale (VAS) for at least 4 of the 14 days in the run-in period, but no more than 60 mm on the VAS on more than 10 days of the 14-day run-in period. Exclusion criteria included hypersensitivity to asimadoline or opiate agonists; alcoholics or substance abusers, previous gastrointestinal surgery (except cholecystectomy, appendectomy or hysterectomy); structural or metabolic conditions that affect the gastrointestinal system; clinically significant abnormal laboratory values at screening visit; unable to withdraw medications that alter gastrointestinal transit, that inhibit CYP 3A4 and 2D6, benzodiazepines or any analgesics.

Of the 155 initial subjects, 30 failed the screen, 13 failed randomization, 9 withdrew consent, 3 had a concomitant illness, 2 were lost to follow-up, and 1 was withdrawn after randomization. 97 subjects completed the study.

The protocol was IRB approved, and written informed consent was obtained from all participants prior to enrollment in the study.

Study Protocol

At the screening visit, an interview, physical examination, EKG, standard laboratory tests, Bowel Disease Questionnaire [BDQ (Hahn et al., (1998) *Dig. Dis. Sci.* 43, 27145-2718)], Hospital Anxiety and Depression Scale [HADS (Zigmond & Snaith (1983) *Acta Psychiatr Scand.,* 67(6), 361-70)] and Quality of Life questionnaire [IBS QoL (Patrick et al., (1998) *Dig Dis Sci.,* 43, 400-11)] were obtained, and patients received diaries to record daily pain and other IBS symptoms. After a 2-week run-in period to establish symptoms at baseline, patients meeting all entry criteria were randomized and received study medication or placebo for the double blind four week treatment period. Allocation of treatment was concealed. Participants returned to the study center after two weeks of treatment and underwent EKG and standard clinical laboratory tests. The patients returned after four weeks of treatment and underwent EKG, standard clinical laboratory tests, fill BDQ, HADS and IBS QoL questionnaires, and daily diaries recording pain and bowel function were collected.

During the double-blind treatment period, patients were instructed to fill in the rating of pain severity on the VAS in the diary whenever they felt pain of at least moderate intensity the first time during a day, before taking the first dose of study medication for that day. Two hours after the intake of the medication, the VAS for pain severity was rated again. If the pain was adequately controlled for the rest of the day, this was recorded in the diary. If the pain was not adequately controlled, the patients were allowed to re-medicate (0.5 mg-1.0 mg), but not earlier than four hours after the previous dose. Patients were allowed to take up to two tablets at a time, up to four times a day.

Bowel movement frequency, consistency [Bristol Stool Form Scale (Heaton et al., (1991) *Gut,* 32(1), 73-9)], daily ease of passage [7 point adjectival scale (Coulie et al., (2000) *Gastroenterology,* 119, 41-50)], and daily adequate relief (Camilleri et al., (2000) *Lancet,* 355, 1035-40) of IBS pain and discomfort (a binary global endpoint) were also collected.

Safety Monitoring

Adverse effects were monitored at the study site daily, and patients were given telephone numbers to contact the study investigators to report any side effects. A follow-up visit was held 2 weeks after the end of the double-blind treatment period to follow-up any abnormalities observed in the previous visits and to undergo a physical examination and repeat BDQ.

Data Analysis

The primary endpoint for analysis was the average reduction in pain severity 2 hours after first dose on each day that the participant experienced at least moderate pain. In essence, the change in pain intensity before and two hours after the first dose on each day with at least 30 mm on the VAS was recorded. For each of these days, the pain reduction of the first dose was calculated: Pain Intensity Difference (PID)= $Pain_{2h}-Pain_{0h}$. The average pain reduction on these days was calculated by: first summing up all the PID over the treatment period and dividing this result by the number of days with pain when medication was used. Secondary endpoints were maximum pain during each day (five point VAS), daily frequency of bowel movements (number), daily consistency of bowel movements (Bristol stool scale), daily ease of passage (7 point adjectival scale), daily adequate relief of IBS pain and discomfort (global endpoint, analyzed as both a continuous proportion of days per subject and as a discrete nominal response, >50% of days with adequate relief), and also the BDQ, HADS, and irritable bowel syndrome quality of life (IBS-QoL) were assessed at the beginning and end of the study.

Statistical Analysis

The treatment effects on the primary and secondary endpoints were assessed using an analysis of covariance (ANCOVA) incorporating relevant covariates (e.g. age, baseline pain severity VAS score, proportion of days with pain and baseline HAD anxiety score for the analysis of pain intensity differences). Secondary analyses were also examined incorporating the predominant bowel function IBS subtype as a covariate along with a treatment by subtype interaction term in the ANCOVA model. For the primary analysis, endpoints an intent to treat (ITT) paradigm was followed imputing missing values for an endpoint using the corresponding overall (subjects with non-missing values) mean value. A consequent adjustment in the error degrees of freedom for the ANCOVA model was made by subtracting one degree of freedom for each missing value imputed in order to obtain an appropriate residual error variance for testing treatment effects: Summary values are reported as median (IQR) or mean (±SE) as indicated.

Results

Baseline Symptoms and Demographics

Sixty subjects were randomized to on-demand treatment with asimadoline, and forty subjects were randomized to placebo as shown in Table 1A.

TABLE 1A

Demographics of participants

|  | Overall (n = 100) | Asimadoline (n = 60) | Placebo (n = 40) |
|---|---|---|---|
| Age (y) (mean ± SE) | 38 ± 1 range 18-67 | 39 ± 2 range 18-67 | 36 ± 2 range 18-66 |
| IBS subtype† - |  |  |  |
| Constipation-predominant | 27(27%) | 14(24%) | 13(32%) |
| Diarrhea-predominant | 33(33%) | 22(37%) | 11(28%) |
| Alternating bowel pattern | 39(39%) | 23(39%) | 16(40%) |

†One subject could not be classified.

Tables 1A and 1B summarize characteristics of the subjects entering the four week active part of the trial. The treatment group and the placebo group were comparable for age, IBS subtype, gastrointestinal symptoms, anxiety and depression scores and IBS-related quality of life scores. Based on the baseline BDQ characterization of symptoms and patient history, there were 39 with alternating bowel patterns, 27 with predominant constipation, and 33 with predominant diarrhea (one subject could not be classified); they were approximately equally randomized to the different treatments, except that there were somewhat more IBS-D randomized to asimadoline relative to placebo.

TABLE 1B

Baseline symptoms (median and IQR or mean ± SEM)

|  | Overall | Asimadoline | Placebo |
|---|---|---|---|
| Bowel movement frequency | 1.68 ± 0.11 | 1.66 ± 0.13 | 1.70 ± 0.20 |
| Stool consistency | 3.92 ± 0.12 | 4.06 ± 0.15 | 3.71 ± 0.20 |
| HAD Anxiety | 5.1 ± 0.3 | 4.7 ± 0.3 | 5.8 ± 0.4 |
| HAD Depression | 2.0 ± 0.2 | 2.0 ± 0.3 | 2.0 ± 0.3 |
| IBS QoL score (mean, SE) | 25.8 ± 1.3 | 25.96 ± 1.8 | 25.54 ± 1.9 |
| Pain (VAS 100 mm) | 37.2 (27.1-49.5) | 37.2 (29.6-51.5) | 37.7 (23.8-44.6) |
| Bloating (VAS 100 mm) | 35.3 (26.1-49.1) | 34.8 (27.2-49.7) | 40.7 (22.8-47.5) |
| Flatulence (VAS 100 mm) | 31.0 (21.7-45.7) | 31.8 (25.2-43.4) | 28.6 (17.9-47.2) |
| Urgency (VAS 100 mm) | 25.1 (15.0-38.4) | 26.1 (16.2-40.4) | 22.2 (14.0-38.2) |
| Severity of most intense pain episode of day (0-4) | 1.6 (1.3-2.0) | 1.6 (1.4-2.0) | 1.6 (1.0-2.0) |

Intake of Treatment During the 4-Week Trial

The overall median number of asimadoline or placebo tablets used during the treatment period was 14.5 (IQR=8.0 to 24.5): Placebo median 13.5 (IQR=9.5 to 19.5), asimadoline median 16.5 (IQR=8.0 to 25.5). The number of tablets used per day with pain was 1.62 (1.18-1.83) for asimadoline and 1.43 (1.08-1.88) for the placebo group.

Effect of on-Demand Study Medication on Abdominal Pain in IBS Subgroups According to Predominant Bowel Pattern A significant treatment by subtype interaction was detected (p=0.004) for delta pain intensity scores. There were larger deltas in pain score for IBS-A subjects assigned to asimadoline relative to placebo treatment. The pairwise comparisons (unadjusted) indicated significant differences in IBS-A (p=0.003), confirming that asimadoline was significantly better than placebo in alternators (see Table 2a, b, and c and FIG. 1A). No treatment by IBS subtype interaction effects were detected for the proportion of days with adequate relief (see FIG. 1B), though IBS-C subjects had substantially smaller proportions with adequate relief than the other two subtypes (i.e. an overall main effect of subtype, p=0.001, was detected). Thus, the drug appears to be more effective in relief of symptoms in IBS-A.

Figure 2:
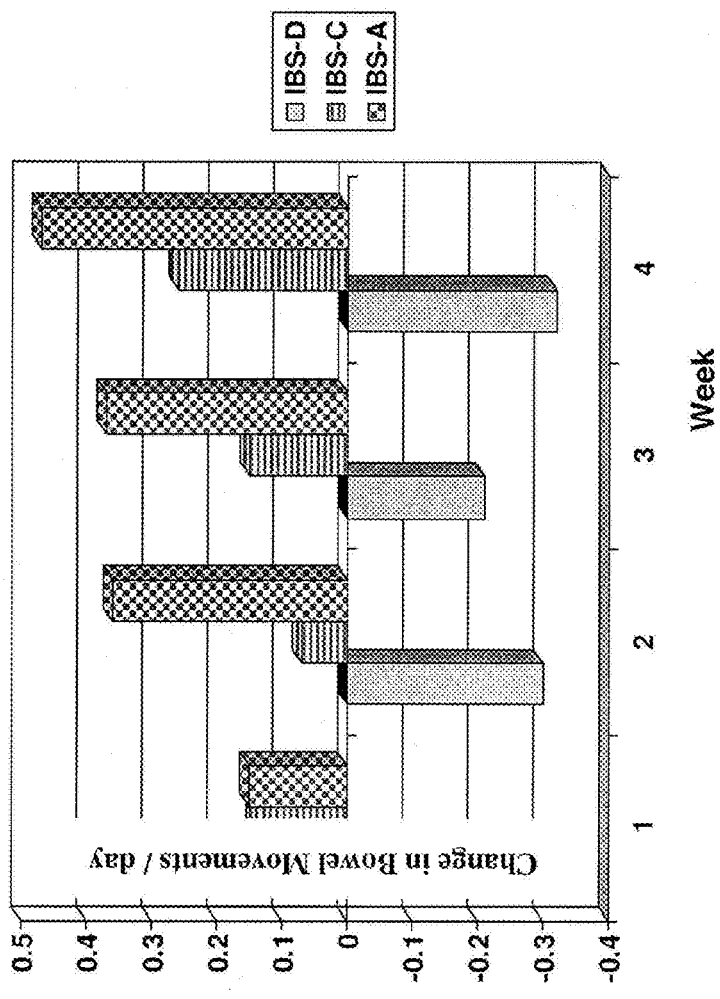
FIG. 2 depicts the change in bowel movements per day against time in weeks of on-demand treatment with asimadoline for the IBS-A, IBS-C and IBS-D subtypes. Corrections were made to subtract the change in the placebo treated groups. This figure supports the hypothesis that asimadoline produces a normalization of bowel function.

Bowel function in the different subtypes was analyzed after correcting for a placebo change from baseline, and is shown as FIG. 2. Change in bowel movements per day is plotted against time in weeks. There was an increase in bowl movements per day for both IBS-C and IBS-A, and a decrease in IBS-D, indicating that asimadoline was normalizing bowel function in the various IBS subtypes.

group, except for the larger number of gastrointestinal events reported in the placebo group.

TABLE 3

| | Adverse events (%) | |
|---|---|---|
| | Asimadoline | Placebo |
| Musculoskeletal | 6.67 | 5.00 |
| Central and peripheral nervous system | 48.33 | 50.00 |
| Psychiatric | 15.00 | 12.50 |
| Gastrointestinal | 16.67 | 30.00 |
| Genitourinary | 1.67 | 5.00 |
| Respiratory | 33.33 | 37.50 |
| Body as a whole | 15.00 | 5.00 |

In this study, an effect on IBS-A was observed when the patients were analyzed by subtype. The analysis showed greater change in pain score with asimadoline versus placebo in IBS patients with alternating bowel function. Asimadoline was well tolerated, with no significant adverse effects noted.

TABLE 2

A. Bowel function at baseline based on predominant bowel function by questionnaire

| | IBS-C | IBS-D | IBS-A |
|---|---|---|---|
| Age (mean ± SE) | 36.9 ± 1.9 | 39.3 ± 2.5 | 37.2 ± 2.0 |
| Mean # daily stools | 1.3 ± 0.2 | 2.1 ± 0.2 | 1.6 ± 0.2 |
| Mean stool form | 3.3 ± 0.3 | 4.6 ± 0.2 | 3.8 ± 0.2 |
| Mean ease of passage | 4.1 ± 0.1 | 4.7 ± 0.1 | 4.3 ± 0.1 |
| Mean proportion stools with complete evacuation | 0.31 ± 0.05 | 0.60 ± 0.05 | 0.40 ± 0.05 |

B. Change in bowel function on treatment compared to baseline based on predominant bowel function

| | IBS-C | | IBS-D | | IBS-A | |
|---|---|---|---|---|---|---|
| | Asimadoline | Placebo | Asimadoline | Placebo | Asimadoline | Placebo |
| Δ mean # stools | −0.1 ± 0.1 | −0.2 ± 0.2 | −0.3 ± 0.1 | −0.1 ± 0.1 | 0.0 ± 0.1 | −0.3 ± 0.15 |
| Δ mean stool form | 0.0 ± 0.2 | 0.3 ± 0.2 | −0.1 ± 0.2 | 0.0 ± 0.2 | 0.2 ± 0.2 | 0.0 ± 0.2 |
| Δ mean ease of passage | −0.1 ± 0.1 | −0.1 ± 0.1 | −0.1 ± 0.1 | 0.0 ± 0.1 | 0.0 ± 0.1 | 0.0 ± 0.1 |

C. Symptoms during treatment in IBS subgroups by predominant bowel pattern (mean ± SE)

| | IBS-C | | IBS-D | | IBS-A | |
|---|---|---|---|---|---|---|
| | Asimadoline | Placebo | Asimadoline | Placebo | Asimadoline | Placebo |
| Number | 14 | 13 | 22 | 11 | 23 | 16 |
| Δ Pain intensity (mm) | 23.8 ± 4.0 | 20.9 ± 3.9 | 25.0 ± 2.9 | 37.5 ± 6.5 | 37.8 ± 3.7* | 22.0 ± 3.0* |
| Proportion of days with adequate relief of symptoms | 0.11 ± 0.07 | 0.18 ± 0.07 | 0.45 ± 0.08 | 0.50 ± 0.11 | 0.46 ± 0.08 | 0.37 ± 0.10 |

*Unadjusted p = 0.003

Anxiety and Depression Response

Anxiety score was modestly affected by asimadoline treatment (p=0.053), but the numerical differences are small (see Table 1B).

Adverse Events

There were no serious clinical or laboratory adverse events. Adverse events reported more than three times were grouped into the categories shown in Table 3 and were similar in each Example 2

Fixed-Dose Administration of Asimadoline is Effective for Treating IBS-D and IBS-a A 12-week, randomized, double-blind, dose-ranging, placebo-controlled study evaluating the effects of a fixed dose of asimadoline (0.15 mg, 0.5 mg or 1.0 mg b.i.d.) or identical appearing placebo on improvement of pain and gastrointestinal symptoms in participants with IBS was performed.

Study Population and Protocol

Diarrhea-predominant (IBS-D), constipation-predominant (IBS-C), and alternating IBS (IBS-A) patients were recruited from 120 sites in the United States. Patients underwent a two week screening period to ensure adequate symptoms and compliance with the interactive voice response system (IVRS) data collection system, followed by twelve weeks of treatment and a four week follow-up period. Patients received identical appearing placebo, 0.15 mg, 0.5 mg or 1.0 mg asimadoline tablets b.i.d. for the 12 week treatment period. During screening, treatment and follow-up patients entered data every day on the IVRS.

The primary endpoint was the number of months a patient was a responder for adequate relief, where the primary measure was the question, "In the past 7 days have you had adequate relief of your IBS pain or discomfort?" This measure was asked once every 7 days and a monthly responder replied "yes" at least 3 weeks per month. Numerous secondary endpoints, abdominal pain or discomfort, stool frequency, urgency, bloating, stool consistency, adequate relief of IBS symptoms and straining were also collected. Additionally, adverse clinical events, laboratory test data and electrocardiograms (ECGs) were collected.

Baseline Symptoms and Demographics

A total of 596 subjects were randomized. Approximately 33% of the subjects were characterized by prospectively defined criteria as IBS-D, 37% IBS-C and 31% IBS-A. 445 subjects were randomized to dose-ranging treatment with asimadoline, and 151 subjects were randomized to placebo. 451 subjects completed the twelve week active part of the trial as well as the four week follow-up period. Of those who completed the trial, 344 subjects were randomized to different doses of asimadoline, and 107 subjects were randomized to placebo. Demographic characteristics of the subjects who completed the entire trial are shown in Table 4A.

TABLE 4A

Demographics of participants

|  | Placebo | Asimadoline | | |
|---|---|---|---|---|
|  |  | 0.15 mg | 0.5 mg | 1.0 mg |
| Age | 48.3 | 46.6 | 47.3 | 49.8 |
| Female | 78.9% | 79.5% | 85.1% | 75.4% |
| Race |  |  |  |  |
| White | 85.7% | 87% | 73.6% | 90.8% |
| Black | 8.2% | 10.3% | 17.6% | 7% |
| IBS subtype |  |  |  |  |
| IBS-D | 36.7% | 30.8% | 27.7% | 33.8% |
| IBS-A | 22.4% | 33.6% | 31.1% | 38.0% |
| IBS-C | 40.8% | 34.9% | 39.9% | 30.3% |

Tables 4A and 4B summarize characteristics of the subjects who completed the twelve week active part of the trial. The three treatment groups and the placebo group were generally comparable for age, gender, IBS subtype, pain scores, as well as frequency, consistency and urgency of bowel movements. Based on the baseline BDQ characterization of symptoms and patient history, there were 142 with alternating bowel patterns, 164 with predominant constipation, and 145 with predominant diarrhea. The subjects were approximately equally randomized to the different treatments, except that there were somewhat more IBS-A randomized to different doses of asimadoline relative to placebo.

TABLE 4B

Baseline symptoms

|  |  | Asimadoline | | |
|---|---|---|---|---|
| Symptom | Placebo | 0.15 mg | 0.5 mg | 1.0 mg |
| Pain |  |  |  |  |
| D-IBS | 2.112 | 2.061 | 2.054 | 2.008 |
| A-IBS | 2.077 | 2.142 | 2.209 | 2.161 |
| C-IBS | 2.051 | 2.237 | 2.118 | 1.997 |
| Frequency |  |  |  |  |
| D-IBS | 3.6 | 3.8 | 3.9 | 2.9 |
| A-IBS | 2.0 | 1.8 | 1.8 | 2.2 |
| C-IBS | 0.9 | 0.9 | 1.0 | 1.1 |
| Consistency |  |  |  |  |
| D-IBS | 5.2 | 5.1 | 5.1 | 5.1 |
| A-IBS | 3.8 | 4.2 | 3.9 | 4.3 |
| C-IBS | 2.6 | 2.6 | 3.1 | 3.0 |
| Urgency (% days) |  |  |  |  |
| D-IBS | 81.0 | 81.4 | 79.8 | 80.8 |
| A-IBS | 63.4 | 63.7 | 65.2 | 67.3 |
| C-IBS | 45.0 | 50.0 | 49.8 | 50.0 |

Results

Summary

Of the 596 subjects who were randomized, 344 reported baseline pain scores of 2.0 or higher. The pain score was a self reported score on a scale of 0-3, where 0=no pain, 1=mild pain, 2=moderate pain and 3=severe pain Subjects having scores of 2.0 or higher were categorized as having moderate or severe pain. Of the 344 moderate or severe pain subjects, 104 were classified as having IBS-D, 114 IBS-A and 126 IBS-C.

In the subjects with moderate or severe pain, a 17% (23% vs. 40%) improvement in percent number of months with adequate relief was observed with both 0.5 mg (p=0.006) and 1.0 mg (p=0.005) dose levels. Evaluation of subjects by IBS subtype revealed a benefit in IBS-D and IBS-A subjects (compare FIG. 3A to 3B). In IBS-D subjects, a significant increase in percent months with adequate relief was seen with 0.5 mg as compared to placebo (20% vs. 47%, p=0.011) and in IBS-A with 1.0 mg dosing as compared to placebo (27% vs. 50%, p=0.022). In IBS-D subjects, significant improvement in urgency, adequate relief of IBS symptoms, stool frequency, bloating and daily pain was seen with the 0.5 mg dose. Significant improvement in pain was seen by week 3 and persisted throughout all 12 weeks of treatment. Benefit was seen in both female and male patients. No benefit in pain in IBS-C subjects was observed.

Figure 4:
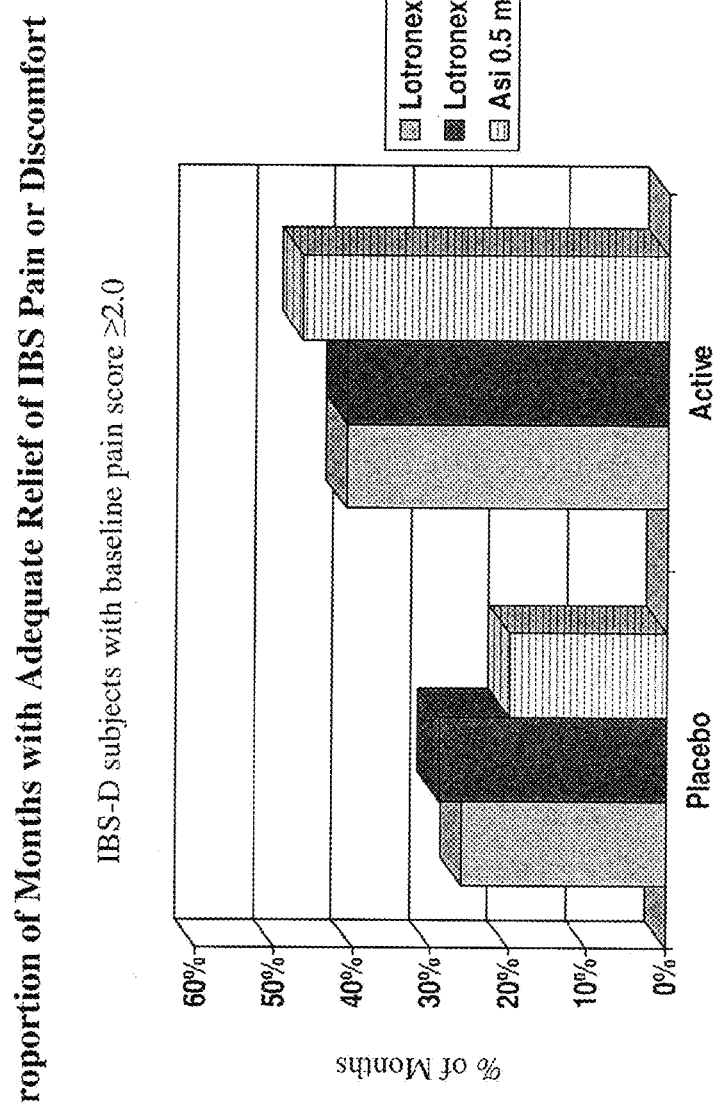
FIG. 4 depicts a comparison of the effect of 0.5 mg asimadoline treatment (b.i.d.) on proportion of months with adequate relief in IBS-D subjects with initial pain scores ≥2.0 to the results from two Phase III trials of LOTRONEX™ (alosetron). Lotronex I refers to data reported in Camilleri, et al., *Lancet* 2000, 355(9209):1035-1040; Lotronex II refers to data reported in Camilleri, et al., *Arch. Intern. Med.* 2001, 161(14):1733-1740. This figure demonstrates that IBS-D patients with initial pain scores ≥2.0 treated with 0.5 mg asimadoline twice a day reported a comparable, or better, improvement of IBS symptoms compared to similar patients treated with LOTRONEX™ (alosetron). The asimadoline trial notably used a more stringent definition of response than the alosetron trials: the asimadoline trial required a response in 3 out of 4 weeks, while the alosetron trials required a response in only 2 out of 4 weeks.
Figures 1, 6:
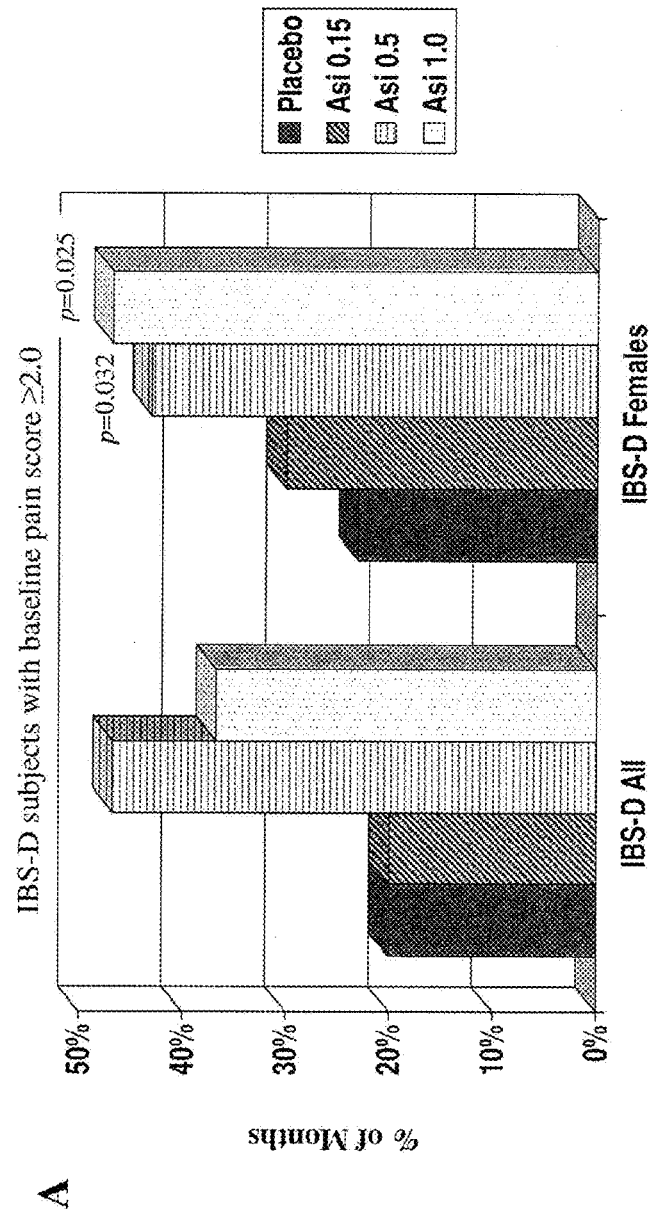
Figures 2, 6:
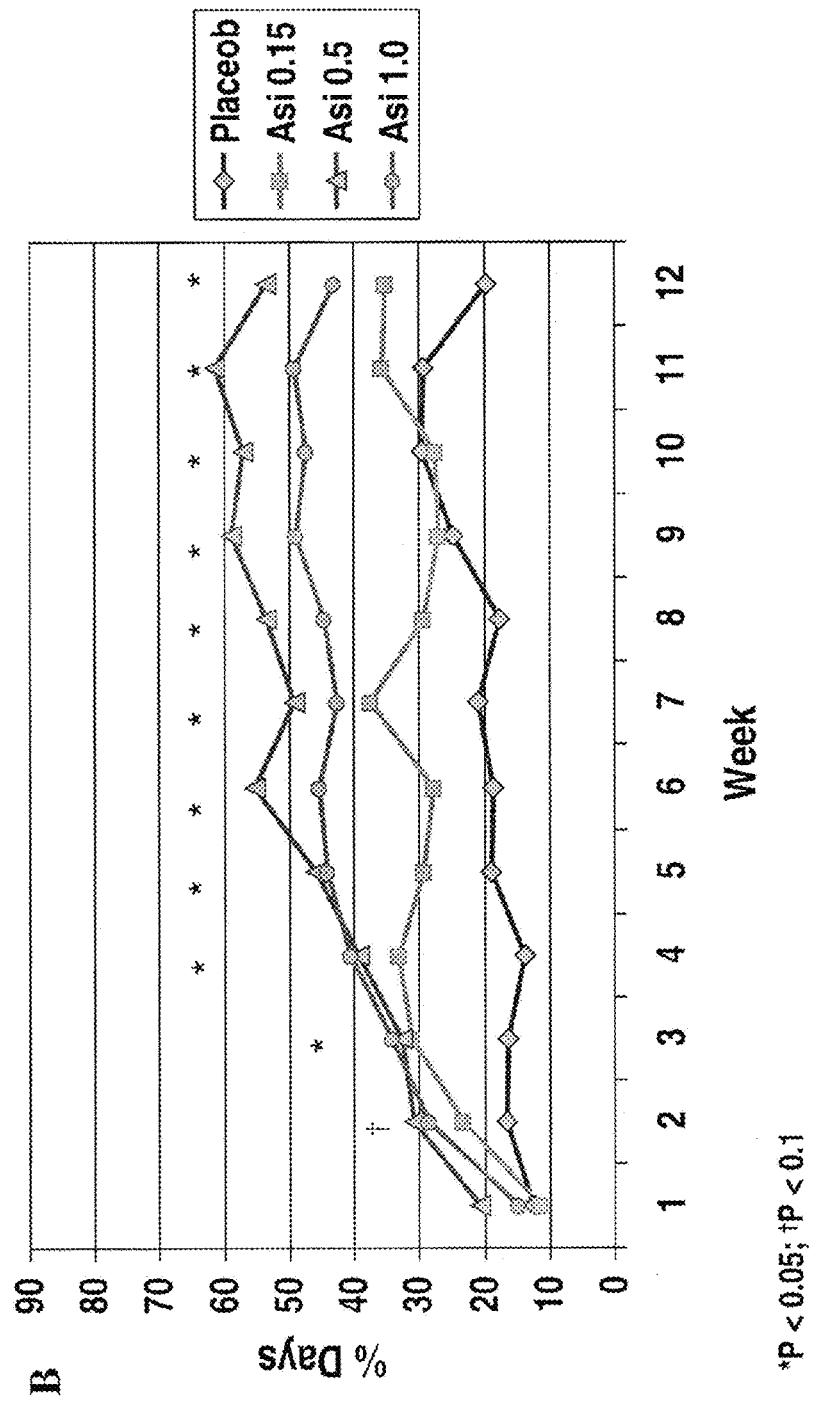
Figures 3, 6:
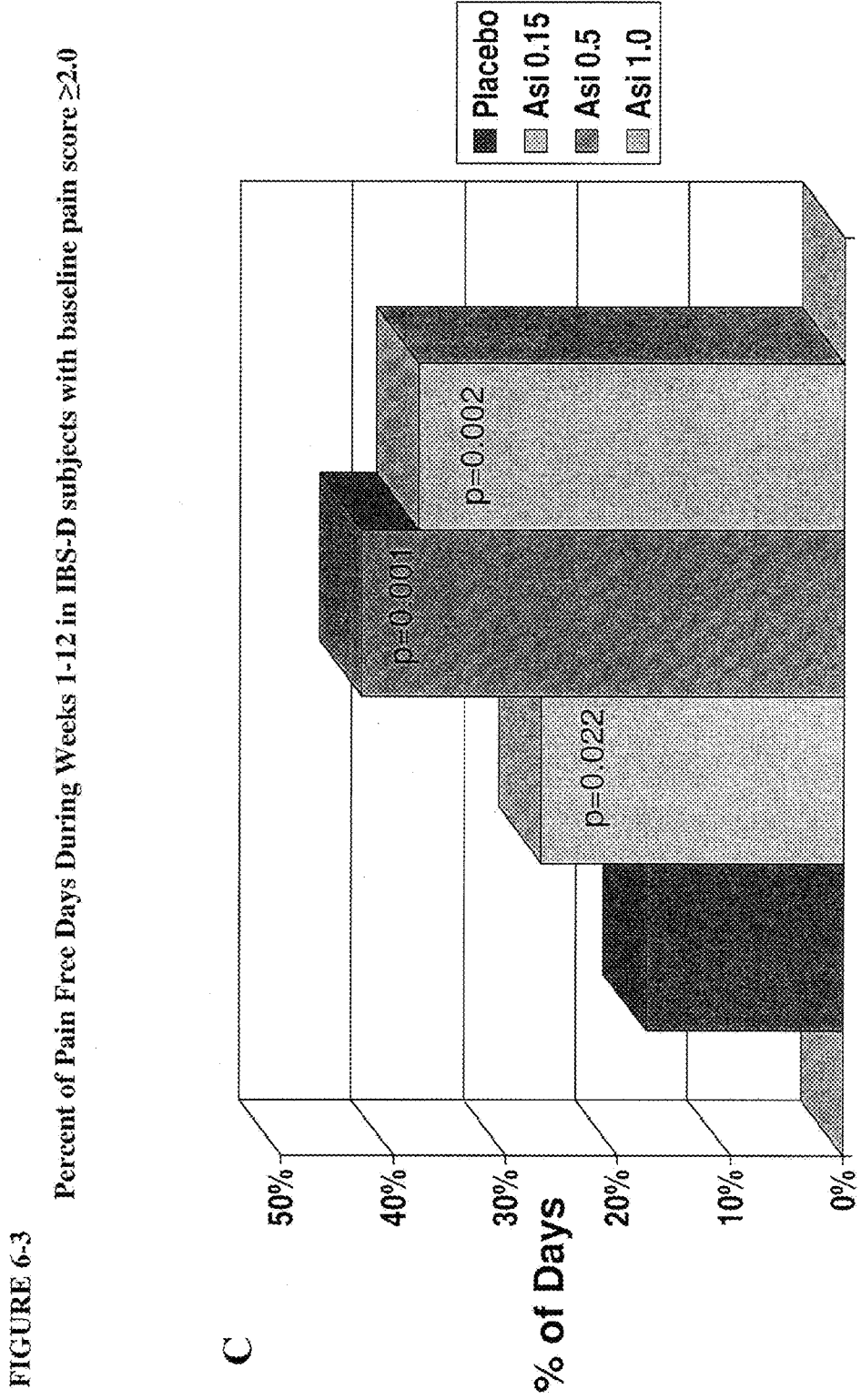

Effect of Fixed-Dose Asimadoline Treatment on Abdominal Pain or Discomfort in IBS Subgroups According to Predominant Bowel Pattern In IBS-D subjects with moderate or severe pain, a statistically significant increase in the proportion of months with adequate relief was seen with 0.5 mg asimadoline as compared to placebo (20% vs. 47%, p=0.011; see FIG. 3B). This improvement compared favorably with results from two Phase III trials of LOTRONEX™ (alosetron) (see FIG. 4). Lotronex I refers to data reported in Camilleri, et al., *Lancet* 2000, 355(9209):1035-1040; Lotronex II refers to data reported in Camilleri, et al., *Arch. Intern. Med.* 2001, 161(14): 1733-1740.

Figure 5:
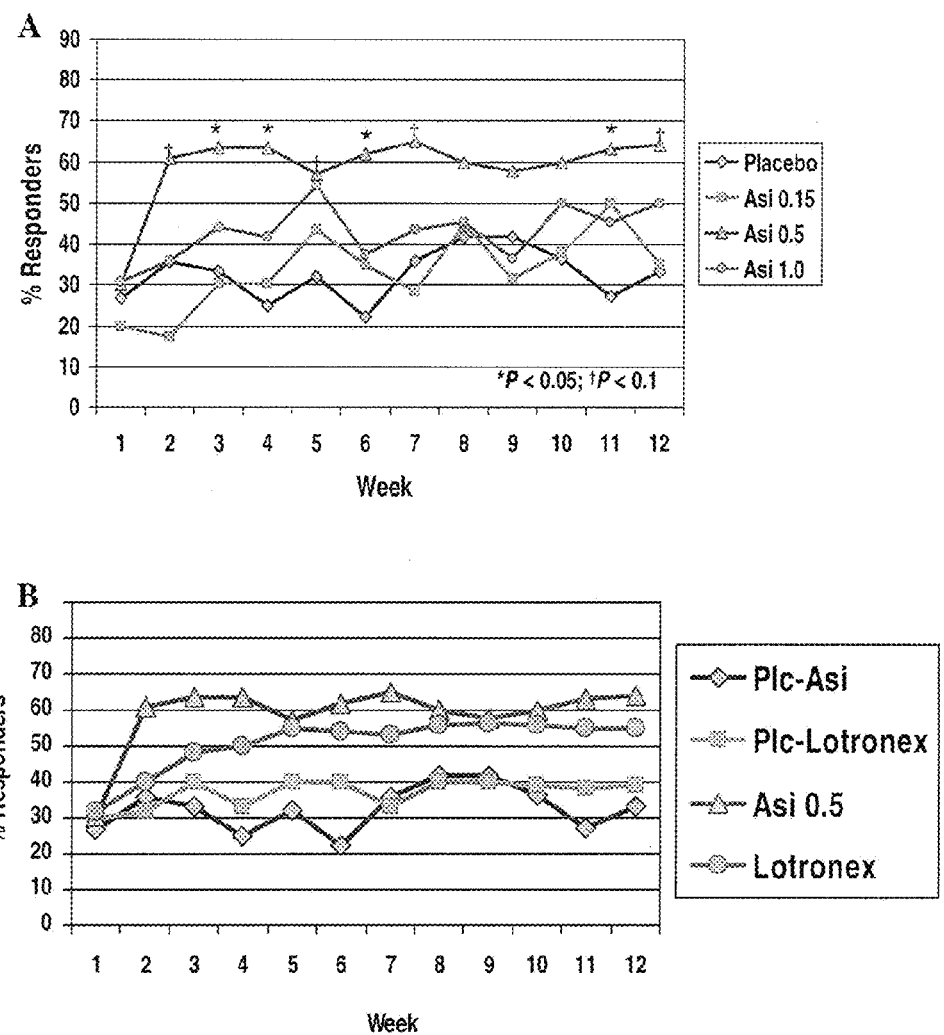
FIGS. 5A and B depict a 12-week time course of the effect of asimadoline treatment on IBS-D subjects with initial pain scores ≥2.0. The data reflect percent responders who reported adequate relief of IBS pain or discomfort in any given week of the trial.
FIG. 5B shows that treatment with 0.5 mg asimadoline resulted in a quicker and more significant improvement of IBS pain or discomfort in IBS-D subjects throughout the 12-week trial than treatment of similar subjects with LOTRONEX™ (alosetron), as reported in Camilleri, et al. Arch. Intern. Med. 2001, 161(14):1733-1740.

The statistically significant effect of 0.5 mg asimadoline treatment relative to placebo was observed throughout most of the 12 weeks of the trial, starting at week 2 (see FIG. 5A). Moreover, the treatment with 0.5 mg asimadoline resulted in a quicker and more significant improvement of IBS pain or discomfort in IBS-D subjects throughout the 12-week trial than treatment of similar subjects with LOTRONEX™ (alosetron), as reported in Camilleri, et al., *Arch. Intern. Med.* 2001, 161(14):1733-1740 (FIG. 5B).

Importantly, the treatment with 0.5 mg asimadoline produced highly similar results in female and male IBS-D subjects (see FIG. 6A). This result is significant because no drug has been approved for treating IBS-D in male patients at the present time.

The number of pain-free days showed an improvement at week 1, which was significant from weeks 2-12 (see FIG. 6B). The early efficacy indicates asimadoline may be useful for both short-term and long-term treatment. An improvement in the percentage of pain-free days was observed for 0.15, 0.5 and 1.0 mg of asimadoline (see FIG. 6C). At 0.5 mg, there was a ~30% improvement in the percentage of pain-free days over placebo. This is much higher than the 10% improvement in the percentage of pain-free days seen with LOTRONEX™, as reported in Bardhan et al., *Aliment Pharmacol Ther* 2000; 14:23-34.

Figures 1, 8:
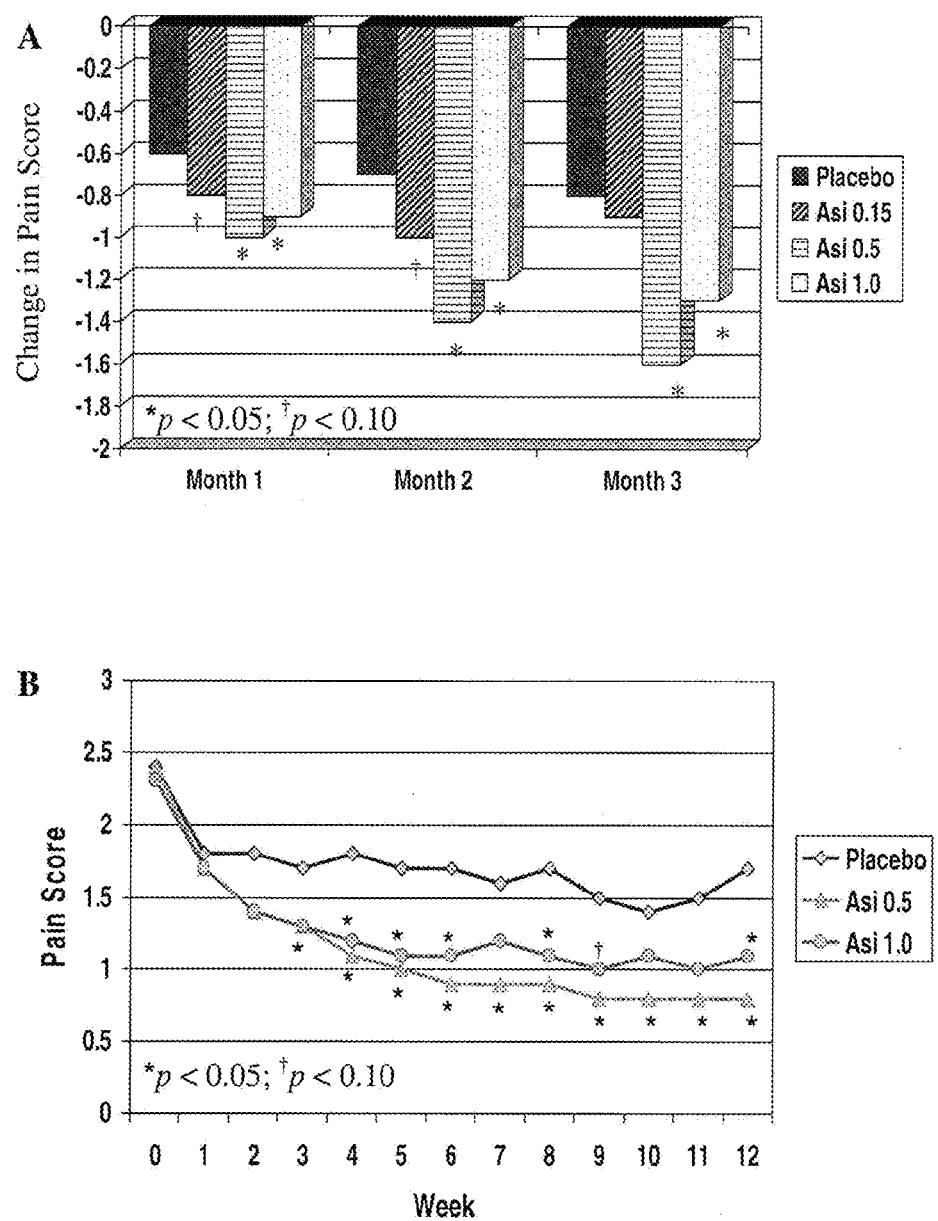
Figures 2, 8:
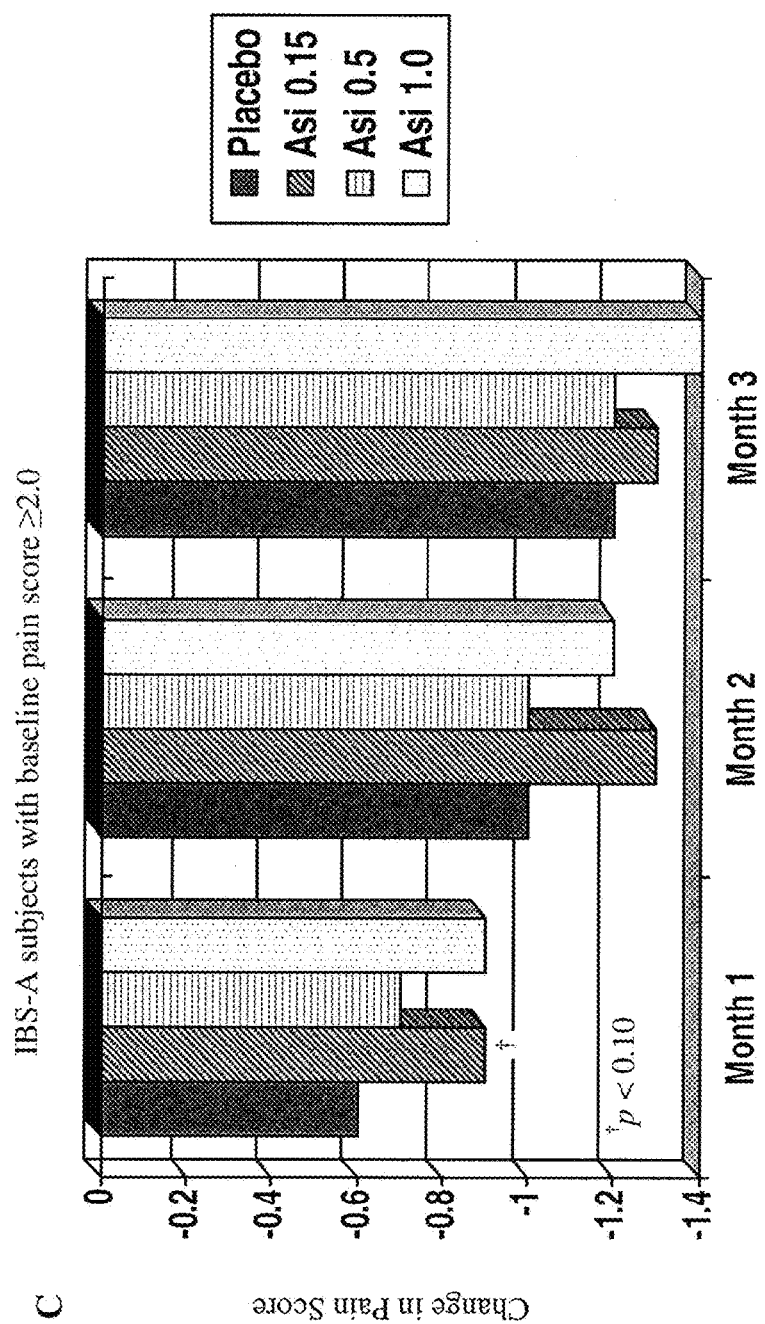
Figure 9:
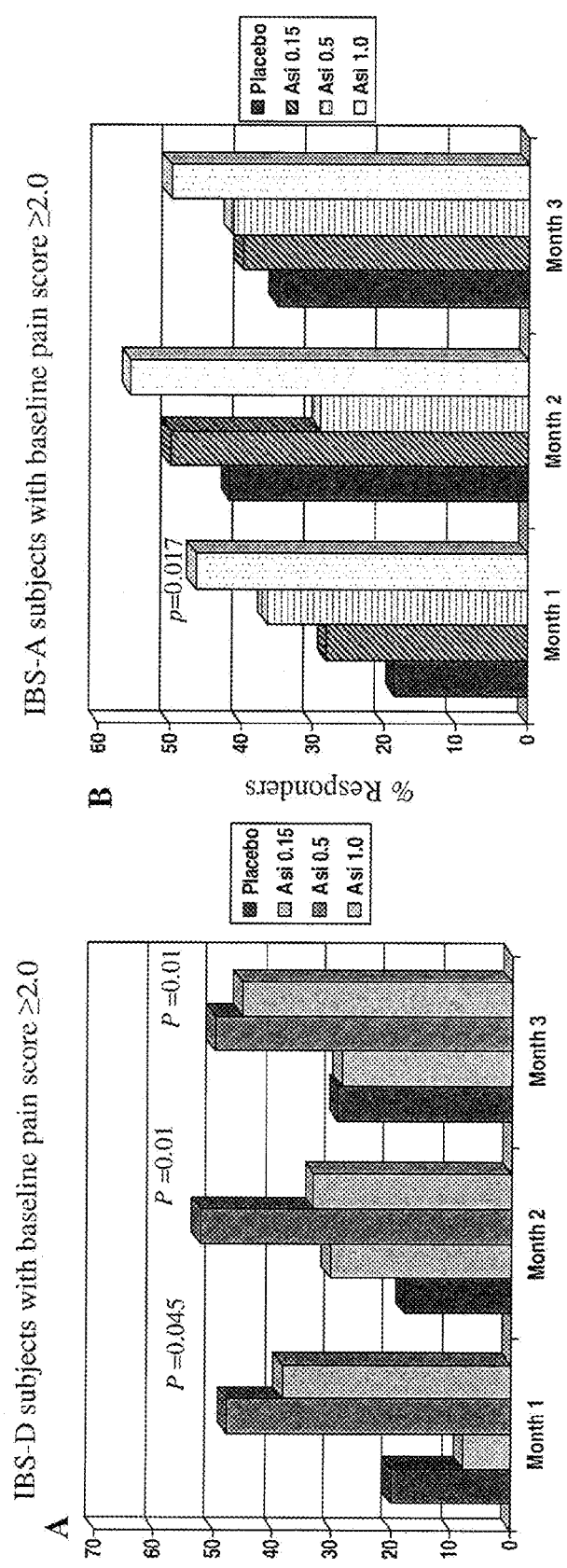
FIGS. 9A and B depict percentages of monthly responders who reported adequate relief of pain or discomfort associated with IBS.
FIG. 9B shows a statistically significant increase in the percentage of IBS-A monthly responders with baseline pain scores ≥2.0 treated with 1.0 mg asimadoline in the first month of treatment.

A statistically significant improvement in the pain scores was observed every week (starting at week 3) and every month in IBS-D subjects receiving 0.5 mg asimadoline (see FIGS. 8A and B). Similarly, a statistically significant improvement in the pain scores was observed every month and in six of the twelve weeks of the trial in IBS-D subjects receiving 1.0 mg asimadoline (see FIGS. 8A and B). In accordance with these results, a statistically significant increase in the percentage of IBS-D monthly responders treated with 0.5 mg asimadoline was observed in all three months of treatment (20% vs. 48%, $p=0.045$ in month 1 and 18% vs. 52%, $p=0.010$ in month 2 and 27% vs. 50%, $p=0.010$ in month 3; see FIG. 9A). No statistically significant improvement in the pain scores was observed in IBS-A subjects at these dosages (FIG. 8C).

Figure 7:
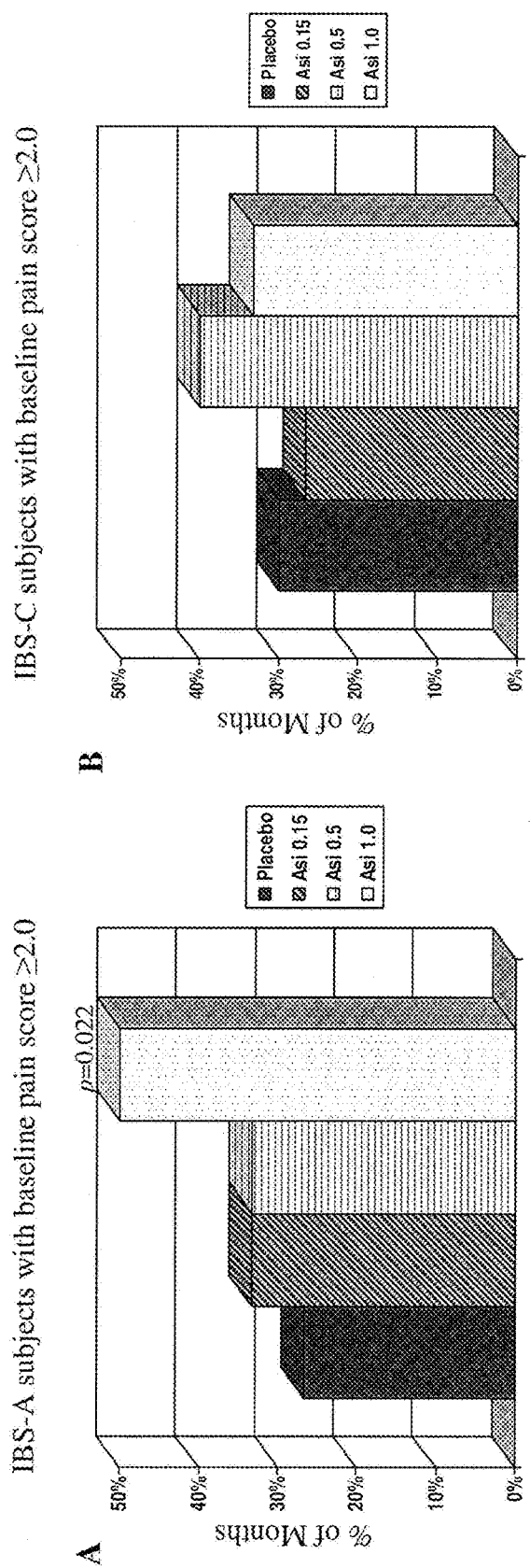
FIGS. 7A and B depict the proportion of months with adequate relief of pain or discomfort associated with IBS in IBS-A and IBS-C subjects with initial pain scores ≥2.0.
FIG. 7B shows results from subjects with IBS-C. These figures demonstrate a statistically significant effect in IBS-A subjects treated with 1.0 mg asimadoline and no significant improvement in IBS-C subjects.

In IBS-A subjects with moderate or severe pain, a statistically significant increase in the proportion of months with adequate relief was seen with 1.0 mg as compared to placebo (27% vs. 50%, $p=0.022$; see FIG. 7A). Consistent with that result, a statistically significant increase in the percentage of IBS-A monthly responders treated with 1.0 mg asimadoline was observed in the first month of treatment (19% v. 46%, $p=0.017$; see FIG. 9B). No statistically significant effect was seen in the pain scores of IBS-A subjects treated with 1.0 mg asimadoline.

In IBS-C subjects with moderate or severe pain, no statistically significant improvement of abdominal pain or discomfort associated with IBS was observed (see FIG. 7B).

Figure 10:
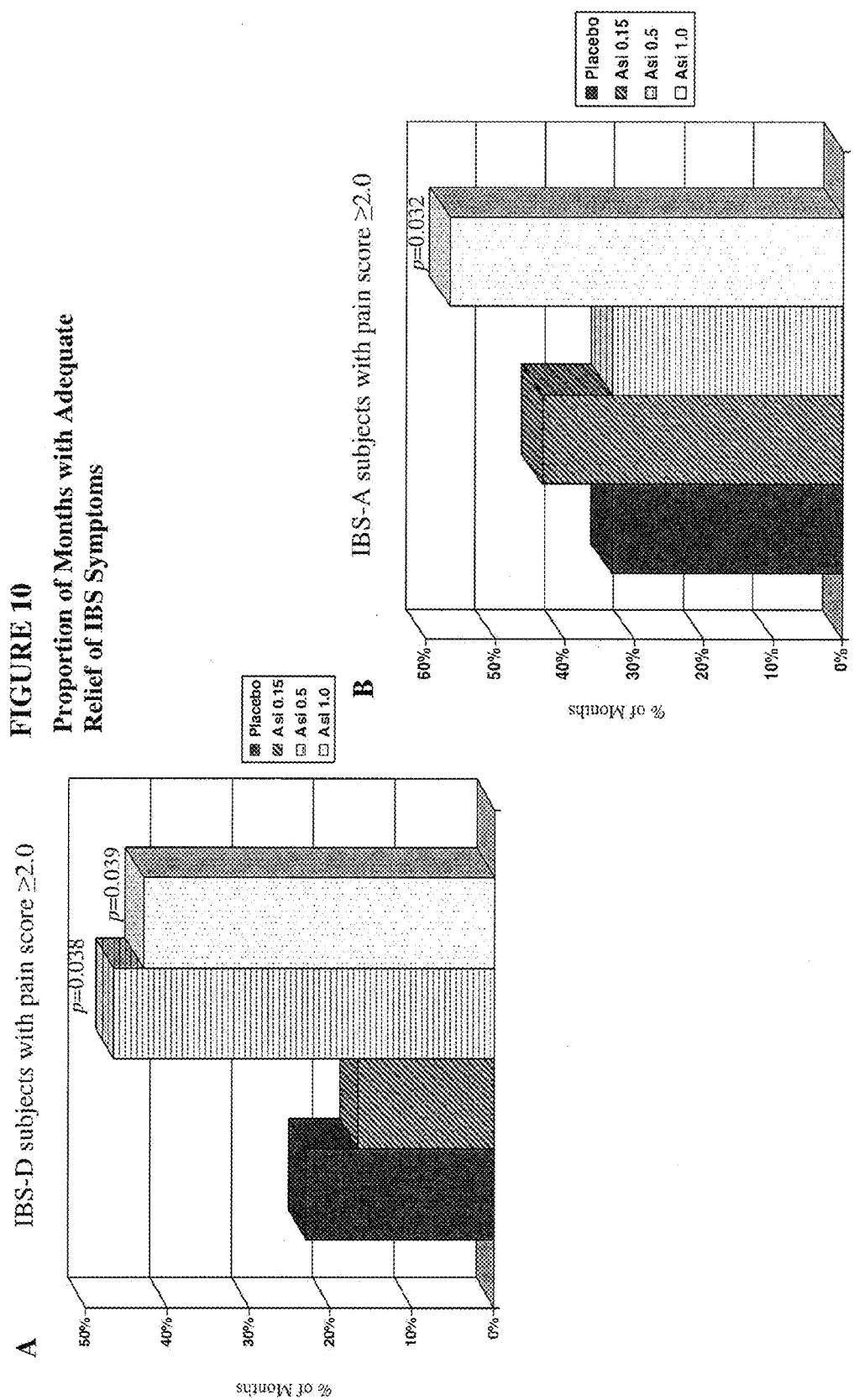
FIGS. 10A and B depict the proportion of months with adequate relief of IBS symptoms in IBS-D and IBS-A subjects with baseline pain scores ≥2.0. IBS symptoms encompass abdominal pain or discomfort, abnormal stool frequency, urgency, bloating, abnormal stool consistency, and other secondary symptoms.

Effect of Fixed-Dose Asimadoline Treatment on IBS Symptoms in IBS Subgroups According to Predominant Bowel Pattern In IBS-D subjects with moderate or severe pain, a statistically significant improvement in adequate relief of IBS symptoms, urgency, stool frequency and bloating was seen with the 0.5 mg dose of asimadoline. Thus, statistically significant improvements in overall IBS symptoms were observed in IBS-D subjects treated with 0.5 mg (23% vs. 47%, $p=0.038$; see FIG. 10A) or 1.0 mg asimadoline (23% vs. 43%, $p=0.039$; see FIG. 10A). Similarly, a statistically significant improvement in overall IBS symptoms was observed in IBS-A subjects treated with 1.0 mg asimadoline (30% vs. 57%, $p=0.032$; FIG. 10B).

Figure 11:
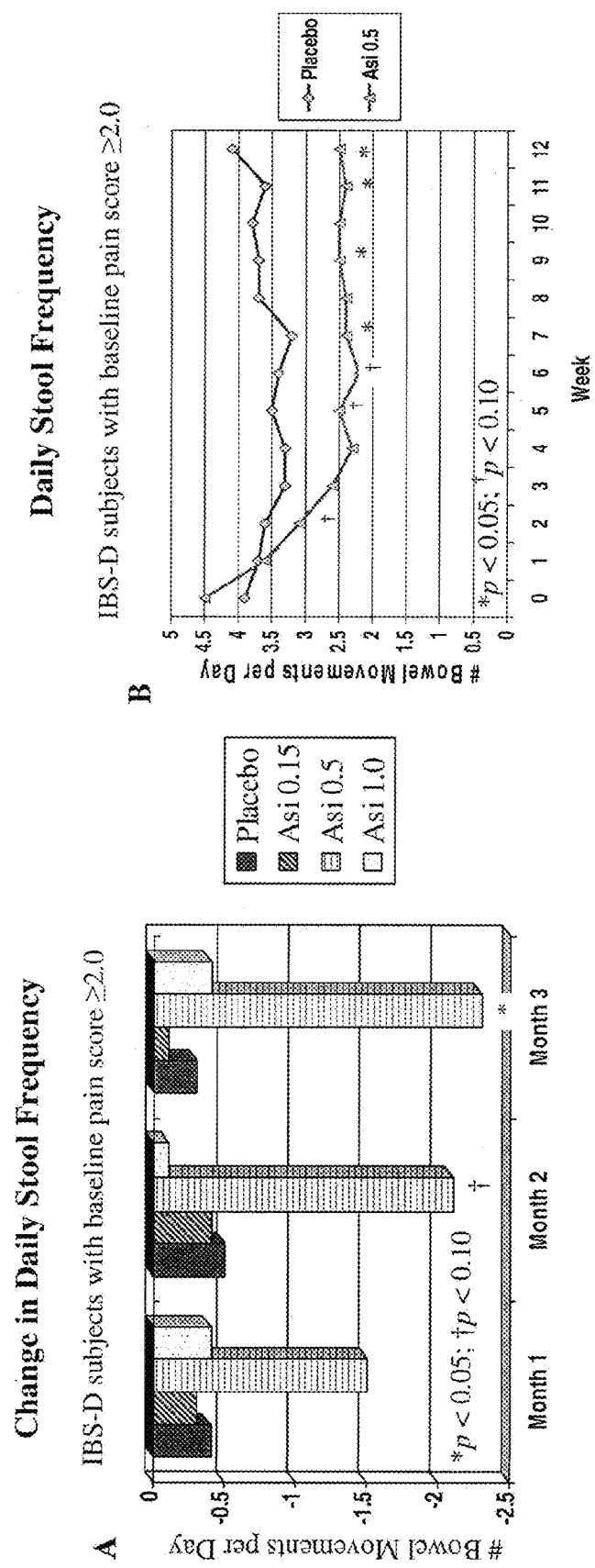
FIGS. 11A and B depict the effect of asimadoline on stool frequency in IBS-D subjects with baseline pain scores ≥2.0.
FIG. 11B demonstrates a weekly time course of improvement in stool frequency in IBS-D subjects treated with 0.5 mg asimadoline.
Figure 12:
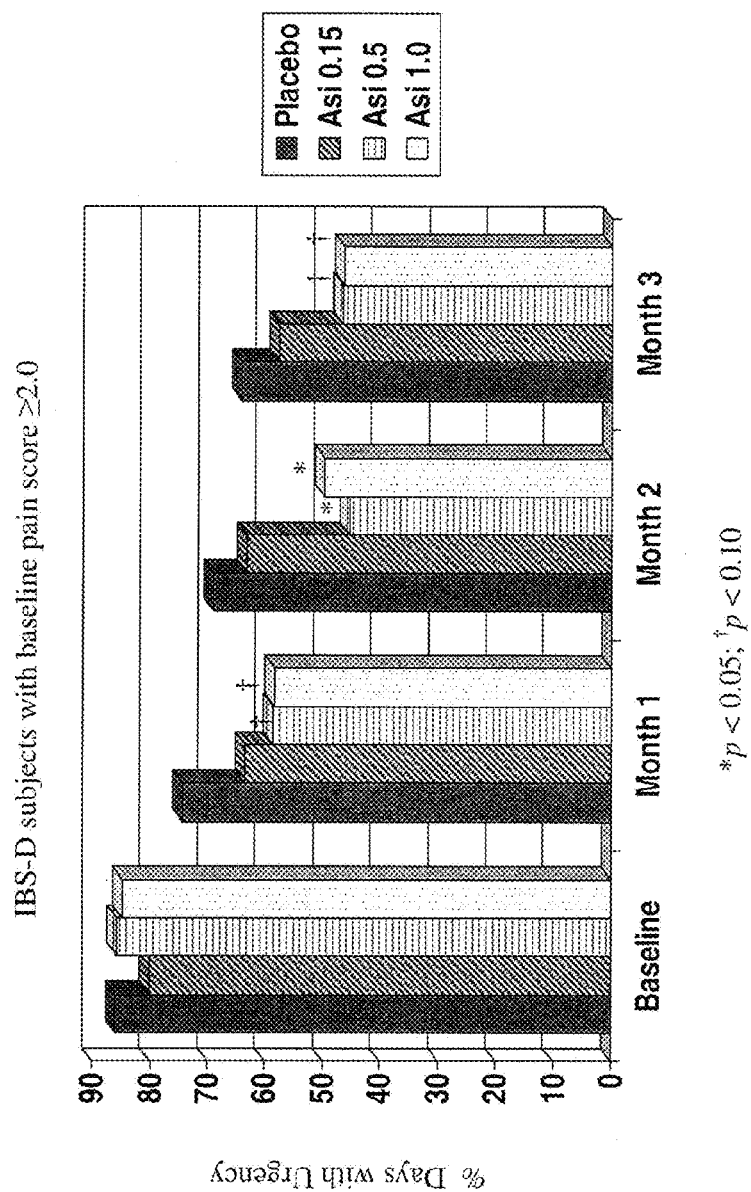
FIG. 12 demonstrates statistically significant reductions in urgency in IBS-D patients with baseline pain scores ≥2.0 treated with 0.5 mg or 1.0 mg asimadoline in all three months of the treatment.
Figure 13:
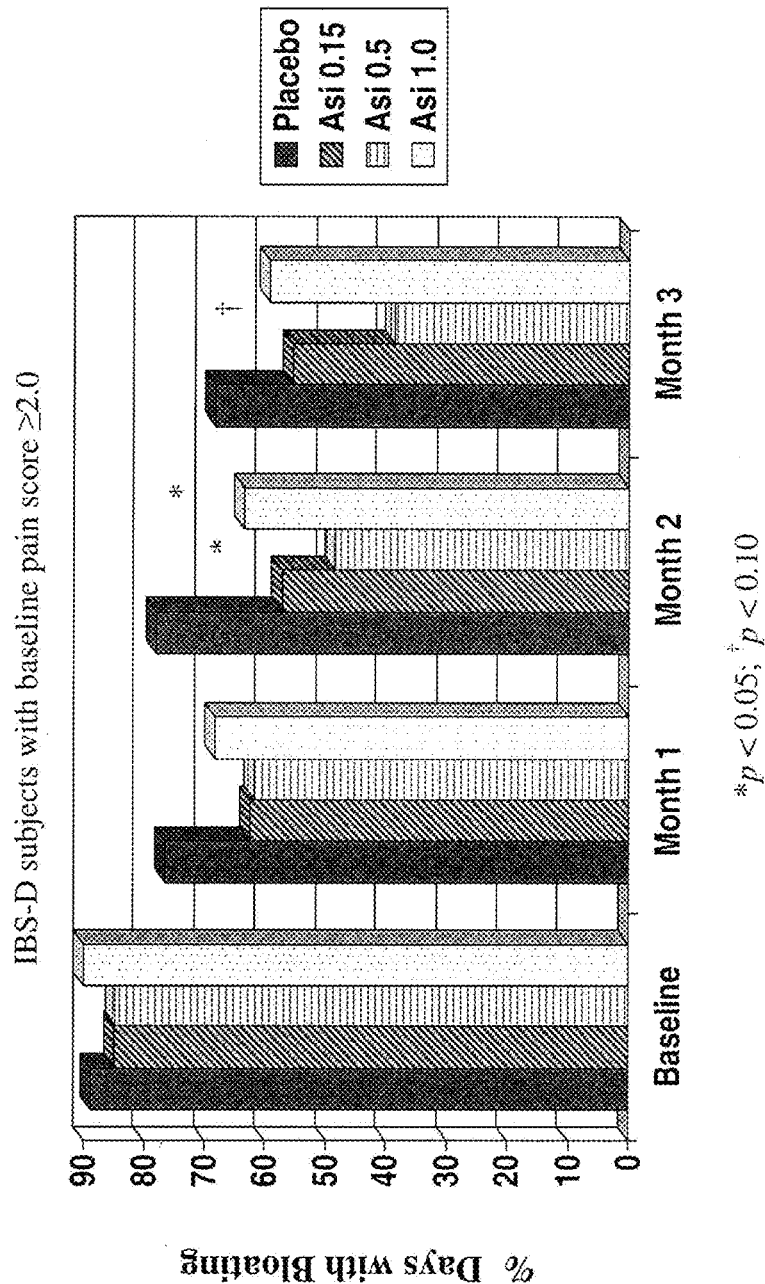
FIG. 13 shows statistically significant reductions in bloating in IBS-D patients with baseline pain scores ≥2.0 treated with 0.5 mg asimadoline in the second and third months of the treatment and in IBS-D patients treated with 1.0 mg asimadoline in the second month of the treatment.

Additionally, a dramatic decrease in daily stool frequency was observed in IBS-D subjects with moderate or severe pain treated with 0.5 mg asimadoline, starting at week 3 and persisting through the end of the treatment (see FIGS. 11A and B). Consistent with that result, statistically significant reductions in urgency were reported in IBS-D patients with moderate or severe pain treated with either 0.5 mg or 1.0 mg asimadoline in all three months of the treatment (see FIG. 12). Significant reductions in bloating were also seen in IBS-D patients with moderate or severe pain treated with 0.5 mg asimadoline in the second and third months of the treatment (see FIG. 13).

Although no statistically significant changes in stool consistency were observed in IBS-D and IBS-C subject at any of the three dosages, asimadoline appeared to soften the stool of IBS-C subjects and harden the stool of IBS-D subjects, thereby normalizing stool consistency (see FIGS. 14A and B).

Adverse Events

No serious clinical or laboratory adverse events related to the treatment were observed. Six adverse events occurred at a frequency of at least 5%. No adverse event showed a dose-dependent increase in rate. Generally, adverse events were more frequent at the lowest dose of asimadoline than at the higher doses. The most common adverse symptoms are summarized in Table 5.

TABLE 5

| | Adverse events (%) | | | |
| --- | --- | --- | --- | --- |
| | | | Asimadoline | |
| Symptom | Placebo | 0.15 mg | 0.5 mg | 1.0 mg |
| Constipation | 4.6 | 12.8 | 10.5 | 7.6 |
| Diarrhea | 7.9 | 13.4 | 5.9 | 11.1 |
| Headache | 7.3 | 9.4 | 4.6 | 5.6 |
| Nausea | 3.3 | 5.4 | 8.6 | 2.8 |
| Sinusitis | 1.3 | 4.7 | 2.6 | 6.3 |
| Abdominal pain | 4 | 5.4 | 4.6 | 4.2 |
| Dizziness | 3.3 | 2.7 | 1.3 | 2.1 |

In this study, treatment with fixed-dose asimadoline produced significant improvement in IBS-D patients with moderate or severe pain across multiple parameters including: pain, urgency and frequency of bowel movements, bloating and overall IBS symptoms. These effects were initially observed during the first month of treatment and persisted throughout the three months of treatment. Benefit was also seen in IBS-A patients on the key endpoints of adequate relief of pain and adequate relief of symptoms. Asimadoline appeared to be well tolerated with no adverse event occurring in a dose-dependent manner.

I claim:

1. A method for treating human subjects having diarrhea-predominant irritable bowel syndrome (IBS-D), comprising administering a pharmaceutical composition comprising 0.3 mg to 5 mg per day of N-methyl-N-[(1S)-1-phenyl-2-((3S)-3-hydroxypyrrolidin-1-yl)ethyl]-2,2-diphenylacetamide or a pharmacologically acceptable salt thereof to said subjects, wherein said administration normalizes bowel motility.

2. The method of claim 1, wherein said administration reduces pain and/or discomfort.

3. The method of claim 1, wherein said administration ameliorates at least one symptom of IBS-D, wherein the symptom is selected from the group consisting of abnormal sense of urgency, abnormal stool frequency, abnormal stool form, abnormal stool passage, passage of mucus and feeling of bloating or abdominal distension.

4. The method of claim 1, wherein the pharmaceutical composition comprises N-methyl-N-[(1S)-1-phenyl-2-((3S)-3-hydroxypyrrolidin-1-yl)ethyl]-2,2-diphenylacetamide hydrochloride.

5. The method of claim 1, wherein 0.3 mg to 2 mg of N-methyl-N-[(1S)-1-phenyl-2-((3S)-3-hydroxypyrrolidin-1-yl)ethyl]-2,2-diphenylacetamide hydrochloride is administered per day.

6. The method of claim 1, wherein 1 mg of N-methyl-N-[(1S)-1-phenyl-2-((3S)-3-hydroxypyrrolidin-1-yl)ethyl]-2,2-diphenylacetamide hydrochloride is administered per day.

7. The method of claim 1, wherein 2 mg of N-methyl-N-[(1S)-1-phenyl-2-((3S)-3-hydroxypyrrolidin-1-yl)ethyl]-2,2-diphenylacetamide hydrochloride is administered per day.

8. The method of claim 1, wherein two doses of 0.5 mg of N-methyl-N-[(1S)-1-phenyl-2-((3S)-3-hydroxypyrrolidin-1-yl)ethyl]-2,2-diphenylacetamide hydrochloride is administered per day.

9. The method of claim 1, further comprising administering an antidiarrheal to the subjects.

10. The method of claim 9, further comprising administering alosetron to the subjects.

11. A method for treating a human subject having IBS-D, comprising orally administering a pharmaceutical composition comprising 0.3 mg to 5 mg per day of N-methyl-N-[(1S)-1-phenyl-2-((3S)-3-hydroxypyrrolidin-1-yl)ethyl]-2,2-diphenylacetamide or a pharmacologically acceptable salt thereof to said subject, wherein said administration normalizes bowel motility.

12. The method of claim 11, wherein said administration reduces pain and/or discomfort.

13. The method of claim 11, wherein said administration ameliorates at least one symptom of IBS-D, wherein the symptom is selected from the group consisting of abnormal sense of urgency, abnormal stool frequency, abnormal stool form, abnormal stool passage, passage of mucus and feeling of bloating or abdominal distension.

14. The method of claim 11, wherein the pharmaceutical composition comprises N-methyl-N-[(1S)-1-phenyl-2-((3S)-3-hydroxypyrrolidin-1-yl)ethyl]-2,2-diphenylacetamide hydrochloride.

15. The method of claim 11, wherein 0.3 mg to 2 mg of N-methyl-N-[(1S)-1-phenyl-2-((3S)-3-hydroxypyrrolidin-1-yl)ethyl]-2,2-diphenylacetamide hydrochloride is administered per day.

16. The method of claim 11, wherein two doses of 0.5 mg of N-methyl-N-[(1S)-1-phenyl-2-((3S)-3-hydroxypyrrolidin-1-yl)ethyl]-2,2-diphenylacetamide hydrochloride is administered per day.

17. The method of claim 11, further comprising administering an antidiarrheal to the subject.

18. A method for treating a human subject having IBS-D, comprising parenterally administering a pharmaceutical composition comprising a therapeutically effective amount of N-methyl-N-[(1S)-1-phenyl-2-((3S)-3-hydroxypyrrolidin-1-yl)ethyl]-2,2-diphenylacetamide or a pharmacologically acceptable salt thereof into said subject, wherein said administration normalizes bowel motility.

19. The method of claim 18, wherein said administration reduces pain and/or discomfort.

20. The method of claim 18, wherein said administration ameliorates at least one symptom of IBS-D, wherein the symptom is selected from the group consisting of abnormal sense of urgency, abnormal stool frequency, abnormal stool form, abnormal stool passage, passage of mucus and feeling of bloating or abdominal distension.

* * * * *